United States Patent [19]

Lum et al.

[11] Patent Number: 5,656,660

[45] Date of Patent: Aug. 12, 1997

[54] COMPOSITIONS AND METHODS FOR TREATING MAST-CELL MEDIATED CONDITIONS

[75] Inventors: Robert T. Lum, Palo Alto; Heinz W. Gschwend, Belmont; Barr E. Bauer, Foster City; Elaine Kuo, San Francisco; Ken Rice, Redwood City, all of Calif.

[73] Assignee: Arris Pharmaceutical Corporation, South San Francisco, Calif.

[21] Appl. No.: 455,286

[22] Filed: May 31, 1995

Related U.S. Application Data

[63] Continuation-in-part of Ser. No. 252,099, Jun. 1, 1994.

[51] Int. Cl.$^6$ .................. A61K 31/335; A61K 31/27; C07C 271/06; C07C 237/20
[52] U.S. Cl. .................... 514/467; 514/478; 514/482; 514/483; 560/32; 560/115; 549/221; 564/161; 564/163; 564/212
[58] Field of Search ................ 560/32, 115; 564/161, 564/163, 212; 549/221; 514/467, 478, 482, 483

[56] References Cited

PUBLICATIONS

Miller et al., "Cloning and Characterization of Complementary DNA for Human Tryptase," *J. Clin. Invest.*, 84:1188–1195 (1989).

Miller et al., "Cloning and Characterization of Complementary DNA for Human Tryptase," *J. Clin. Invest.*, 86:864–870 (1990).

Nair et al., "Litocholic Acid in Human Liver: Identification of ε-Lithocholyl Lysine in Tissue Protein," *Lipids*, 12(11):922–929.

Ochi et al., "Synthetic Studies of Vitamin D$_3$ Analogues from Bile Acids. Part 2. Syntheses of Cholesta–1, 4–dien–and –1, 4, 6–trien–3–ones having a 24–and/or 25–Hydroxylated Side Chain from Lithocholic Acid," *J. Chem. Soc. Perkin Trans. I*, 1(1):161–164 (1979).

Ruoss et al., "Mast Cell Tryptase Is a Mitogen for Cultured Fibroblasts," *J. Clin. Invest.*, 88:493–499 (1991).

Schwartz et al., "Tryptase Levels as an Indicator of Mast–Cell Activation in Systemic Anaphylaxis and Mastocytosis," *N. Engl. J. Med.*, 316:1622–1626 (1987).

Sekizawa et al., "Mast Cell Tryptase Causes Airway Smooth Muscle Hyperresponsiveness in Dogs," *J. Clin. Invest.*, 83: 175–179 (1989).

Sturzebecher et al., "Inhibition of Human Mast Cell Tryptase by Benzamidine Derivatives," *Biol. Chem Hoppe–Seyler*, 373:1025–1030 (1992).

Tam et al., "Degradation of Airway Neuropeptides by Human Lung Tryptase," *Am. J. Respir. Cell Mol. Biol.*, 3:27–32 (1990).

Tidwell et al., "Aromatic Amidines: Comparison of Their Ability to Block Respiratory Syncytial Virus Induced Cell Fusion and to Inhibit Plasmin, Urokinase, Thrombin, and Trypsin," *J. Med. Chem.*, 26: 294–298 (1983).

Tidwell et al., "Suppression of Respiratory Syncytial Virus Infection in Cotton Rats by Bis(5–Amidino–2–Benzimidazolyl)Methane," *Antimicrobial Agents and Chemotherapy*, 26:591–593 (1984).

Vanderslice et al., "Molecular Cloning of Dog Mast Cell Tryptase and a Related Protease: Structural Evidence of a Unique Mode of Serine Protease Activation," *Biochemistry*, 28:4148–4155 (1989).

Vanderslice et al., "Human mast cell tryptase: Multiple cDNAs and genes reveal a multigene serine protease family," *Proc. Natl. Acad. Sci. USA*, 87:3811–3815 (1990).

Wanner et al., "Models of Airway Hyperresponsiveness," *Am. Rev. Respir. Dis.*, 141:253–257 (1990).

Wenzel et al., "Activation of Pulmonary Mast Cells by Bronchoalveolar Allergen Challenge," *Am. Rev. Resp. Dis.*, 141:1002–1008 (1988).

Yamada et al., "Synthesis of 24, 24–Difluoro–25–Hydroxyvitamin D$_3$," *Tetrahedron Letters*, 21: 1859–1862 (1979).

*Primary Examiner*—Joseph Conrad
*Attorney, Agent, or Firm*—Townsend and Townsend and Crew LLP

[57] ABSTRACT

The present invention describes compounds, methods and compositions effective to treat mast cell mediated inflammatory conditions, such as conjunctivitis, asthma and allergic rhinitis. The compounds of the invention comprise novel mono- and di-aminomethylbenzyl, aminobenzyl, guanidylbenzyl and benzyl tryptase inhibitors. The compositions for treating mast cell mediated inflammatory conditions include oral, inhalant and topical preparations as well as devices comprising such preparations.

42 Claims, 3 Drawing Sheets

* DATA OBTAINED FROM A PREVIOUS STUDY THAT INCLUDED THE SAME ANIMALS

COMPOSITIONS AND METHODS FOR TREATING MAST-CELL MEDIATED CONDITIONS

CROSS-REFERENCE TO RELATED APPLICATION

This application is a continuation-in-part application of co-pending U.S. application Ser. No. 08/252,099, filed Jun. 1, 1994.

BACKGROUND OF THE INVENTION

1. Field of the Invention

This invention relates to compositions and methods effective for the prevention and treatment of mast-cell mediated inflammatory disorders. The invention includes compositions and methods effective for the prevention and treatment of inflammatory diseases associated with the respiratory tract, such as asthma and allergic rhinitis. The compositions and methods of the present invention are especially useful for preventing or treating the late phase bronchoconstriction and airway hyperresponsiveness associated with chronic asthma. In addition, the compositions and methods of the present invention have utility in treating other types of immunomediated inflammatory disorders, such as rheumatoid arthritis, conjunctivitis and inflammatory bowel disease, as well as various dermatological conditions.

2. Description of the Background Art

Asthma is a complex disease involving multiple biochemical mediators for both its acute and chronic manifestations. Increasingly, asthma is recognized as an inflammatory disorder (see, e.g., Hood, et al., IMMUNOLOGY 2nd ed., (Benjamin-Cummings 1984). Asthma frequently is characterized by progressive development of hyperresponsiveness of the trachea and bronchi to both immunospecific allergens and generalized chemical or physical stimuli. The hyperresponsiveness of asthmatic bronchiolar tissue is believed to result from chronic inflammation reactions, which irritate and damage the epithelium lining the airway wall and promote pathological thickening of the underlying tissue. Bronchial biopsy studies have indicated that even patients with mild asthma have features of inflammation in the airway wall.

One initiator of the inflammatory sequence is an allergic response to inhaled allergens. Leukocytes carrying IgE receptors, notably mast cells and basophils, but also including monocytes, macrophages, and eosinophils, are present in the epithelium and underlying smooth muscle tissues of bronchi, where they are activated initially by binding of specific inhaled antigens to the IgE receptors. Activated mast cells release a number of preformed or primary chemical mediators of the inflammatory response and enzymes. Furthermore, numerous secondary mediators of inflammation are generated in situ by enzymatic reactions of activated mast cells, including superoxide and lipid derived mediators. In addition, several large molecules are released by degranulation of mast cells: proteoglycans, peroxidase, arylsulfatase B, and notably the proteases tryptase and chymotryptic proteinase (chymase). See DRUG THERAPY OF ASTHMA, pp. 1054–54.

This chemical release from mast cells probably accounts for the early bronchiolar constrictor response that occurs in susceptible individuals after exposure to airborne allergens. The early asthmatic reaction is maximal at around fifteen minutes after allergen exposure; recovery occurs over the ensuing one to two hours. In 25–35% of individuals, the early asthmatic reaction is followed by a further decline in respiratory function which begins within a few hours and is maximal between six and twelve hours post-exposure. This late asthmatic reaction is accompanied by a marked increase in the number of inflammatory cells infiltrating bronchiolar smooth muscle and epithelial tissues, and spilling into the airways. These cells include eosinophils, neutrophils, and lymphocytes, all of which are attracted to the site by release of mast cell derived chemotactic agents. The infiltrating cells themselves become activated during the late reaction phase. The late asthmatic response is believed to be a secondary inflammatory reaction mediated in part by the secretory activity of macrophages.

Tryptase is the major secretory protease of human mast cells and is proposed to be involved in neuropeptide processing and tissue inflammation. Mature human tryptase is a glycosylated, heparin-associated tetramer of heterogenous, catalytically active subunits. See, e.g., Vanderslice et al. Proc. Natl. Acad. Sci. USA 87:3811–3815 (1990); Miller et al. J. Clin. Invest. 86:864–870 (1990); Miller et al. J. Clin. Invest. 84:1188–1195 (1989); and Vanderslice et al. Biochemistry 28:4148–4155 (1989).

Tryptase is stored in mast cell secretory granules. After mast cell activation, human tryptase can be measured readily in a variety of biologic fluids. For example, after anaphylaxis, tryptase appears in the bloodstream, where it remains detectable for several hours. See Schwartz et al., N. Engl. J. Med. 316:1622–1626 (1987). Its appearance has been detected in samples of nasal and lung lavage fluid from atopic subjects challenged with specific antigen. See Castells and Schwartz, J. Allerg. Clin. Immunol. 82:348–355 (1988) and Wenzel, et al., Am. Rev. Resp. Dis. 141:563–568 (1988). Tryptase levels in lung lavage fluid obtained from atopic asthmatics increase after endobronchial allergen challenge. Some smokers of cigarettes have striking elevations of bronchoalveolar lavage fluid tryptase levels compared to nonsmoker control groups, a finding that provides some support for the hypothesis that release of proteinases from activated mast cells could contribute to lung destruction in smoker's emphysema. See Kalenderian, et al., Chest 94:119–123 (1988). In addition, tryptase has been shown to be a potent mitogen for fibroblasts, suggesting its involvement in pulmonary fibrosis and interstitial lung diseases. See Ruoss et al., J. Clin. Invest. 88:493–499 (1991).

Tryptase has been implicated in a variety of biological processes, including degradation of vasodilating and bronchorelaxing neuropeptides (see Caughey, et al., J. Pharmacol. Exp. Ther. 244:133–137 (1988); Franconi, et al., J. Pharmacol. Exp. Ther. 248:947–951 (1988); and Tam, et al., Am. J. Respir. Cell Mol. Biol. 3:27–32 (1990)) and modulation of bronchial responsiveness to histamine (see Sekizawa, et al., J. Clin. Invest. 83:175–179 (1989)). These studies suggest that tryptase possibly increases bronchoconstriction in asthma by destroying bronchodilating peptides.

Additionally, tryptase has been shown to cleave fibrinogen α-chains, as well as high molecular weight kininogen with a possible release of kinins and thus, may play a role with heparin as a local anticoagulant. The ability of tryptase to activate prostromelysin (pro-MMP-3) and procollagenase (pro-MMP-1) via MMP-3 suggests that tryptase also may be involved in tissue inflammation and remodeling. This finding also intimates that tryptase may play a role in joint destruction in rheumatoid arthritis. In addition, tryptase has been shown to cleave calcitonin gene-related peptide. As this peptide is implicated in neurogenic inflammation, tryptase could be a factor in the regulation of flare reaction in cutaneous neurogenic inflammation. See Caughey, *Am. J. Respir. Cell Mol. Biol.* 4:387–394 (1991).

Mast cell mediated inflammatory conditions are a growing public health concern. In particular, asthma has become a common chronic disease in industrialized countries. Therefore, it would be desirable to provide improved compositions and methods for providing effective treatment for these diseases.

SUMMARY OF THE INVENTION

The present invention provides compounds effective to inhibit tryptase activity comprising the structure:

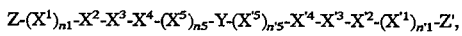

and its pharmaceutically acceptable salts. Y may be arylene or substituted arylene, and Z and Z' are independently

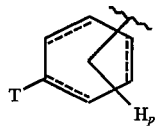

where T is $-CH_2NH_2$ or $-NHC(NH)NH_2$; and p is an integer between 4 and 10 inclusive. $X^1$, $X'^1$, $X^5$ and $X'^5$ are methylene or substituted methylene, and $n_1$, $n'_1$, $n_5$ and $n'_5$ independently are 0 or 1. $X^2$, $X'^2$, $X^4$ and $X'^4$ are selected independently from the group consisting of -NRC(O)-, -NRC(O)NR'-NRC(O)O- -C(O)NR- and -OC(O)NR-, wherein R and R' are selected independently from the group consisting of hydrogen, lower alkyl, substituted lower alkyl, aryl, substituted aryl, aralkyl and substituted aralkyl; and $X^3$ and $X'^3$ are selected independently from the group consisting of cycloalkylene, cycloheteroalkylene, substituted cycloalkylene, and substituted cycloheteroalkylene, lower alkylene and substituted lower alkylene.

Preferred compounds are those wherein Y is phenyl or substituted phenyl, and Z and Z' are 4-aminomethylphenyl, 4-aminomethylcyclohexyl, or 4-guanidylphenyl. More preferred are compounds wherein Y, Z and Z' are as just described and $X^1$, $X'^1$, $X^5$ and $X'^5$ are methylene, $X^2$, $X'^2$, $X^4$ and $X'^4$ are -NHC(O)-, -C(O)NH-, -NHC(O)O-, and -OC(O)NH-, respectively, and $X^3$ and $X'^3$ are ethylene or propylene.

Examples of especially preferred compounds include: bis(p-xylylenediamineglycine)-1,4-benzenedimethanol dicarbamate; bis(p-xylylenediaminesarcosine)-1,4-benzenedimethanol dicarbamate; N,N'-bis(4-aminomethylbenzamidopropylene)-1,4-benzenedimethanol dicarbamate; N,N'-bis(4-aminomethylbenzamidoethylene)-1,4-benzenedimethanol dicarbamate, and N,N'-bis(4-guanidylbenzylaminecarbonylmethylene)-1,4-benzenedimethanol dicarbamate.

The present invention also provides for pharmaceutical compositions of the compounds of the invention. These pharmaceutical compositions can be in a variety of forms including oral dosage forms, inhalable forms, as well as injectable and infusible solutions. When used for the treatment of immunomediated inflammatory skin conditions, the compounds of the present invention are used in combination with a non-toxic, pharmaceutically acceptable topical carrier. The compounds of the present invention can be used in combination with antiinflammatories or other asthma therapies, such as β-adrenergic agonists, anti-inflammatory corticosteroids, anticholinergics, bronchodilators such as methyl xanthenes and the like.

The compounds described herein are useful for the prevention and treatment of immunomediated inflammatory disorders, and particularly those associated with the respiratory tract, including asthma, and particularly the hyperresponsiveness phase associated with chronic asthma, and allergic rhinitis. Thus, the present invention also provides a method for treating immunomediated inflammatory disorders wherein a patient having an immunomediated inflammatory disorder that is susceptible to treatment with a tryptase inhibitor receives, or is administered, a therapeutically effective dose or amount of a compound of the present invention.

DESCRIPTION OF THE PREFERRED EMBODIMENT

I. Definitions

Figure 1:
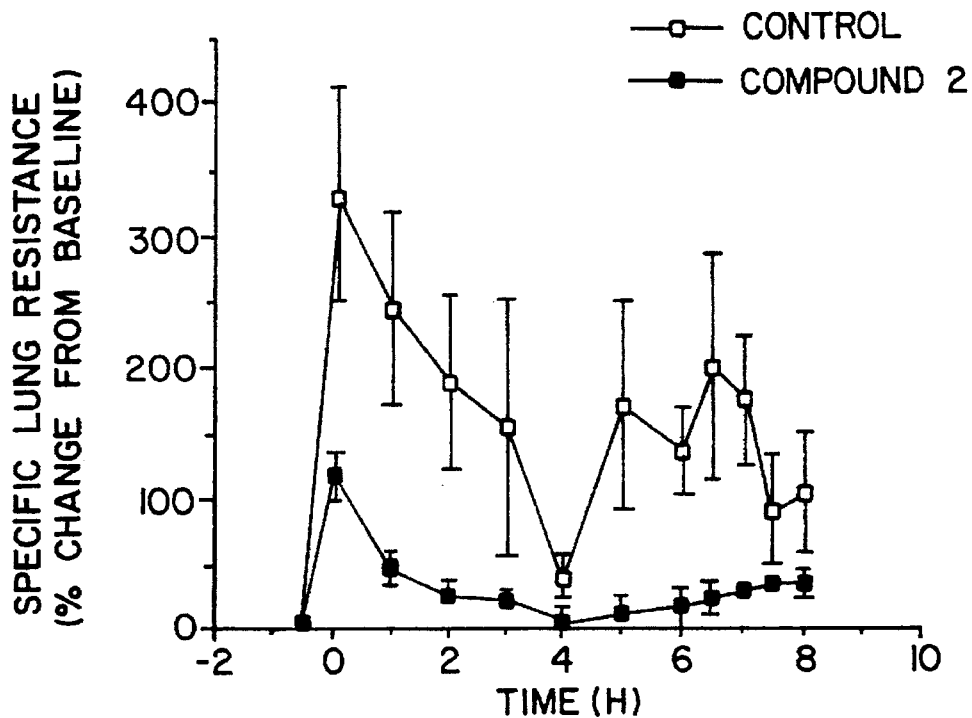
FIG. 1 is a graphical representation of the Specific Lung Resistance (SRL) as a function of time (in hours) of antigen-challenged sheep treated with N,N'-bis(4-guanidylbenzylaminecarbonylmethylene)-1,4-benzenedimethanol dicarbamate, Compound 2 of Table II, and sheep treated with a control.

The following definitions are set forth to illustrate and define the meaning and scope of the various terms used to describe the invention herein.

"Immunomediated inflammatory disorder" includes generally those diseases associated with mast cell mediator release and susceptible to treatment with a tryptase inhibitor. Examples of such disorders include diseases of immediate type hypersensitivity such as asthma, allergic rhinitis, urticaria and angioedema, and eczematous dermatitis (atopic dermatitis), and anaphylaxis, as well as hyperproliferative skin disease, peptic ulcers, inflammatory bowel disorder, ocular and vernal conjunctivitis, rheumatoid arthritis, inflammatory skin conditions, and the like.

"Hyperresponsiveness" refers to late phase bronchoconstriction and airway hyperreactivity associated with chronic asthma. Hyperresponsiveness of asthmatic bronchiolar tissue is believed to result from chronic inflammation reactions, which irritate and damage the epithelium lining the airway wall and promote pathological thickening of the underlying tissue.

"Halogen" refers to fluorine, bromine, chlorine, and iodine atoms.

"Hydroxyl" refers to the group -OH.

"Thiol" or "mercapto" refers to the group -SH.

The term "alkoxyl" denotes the group -OR, where R is lower alkyl, substituted lower alkyl, aryl, substituted aryl, aralkyl or substituted aralkyl as defined below.

The term "alkylthio" denotes the group -SR, where R is lower alkyl, substituted lower alkyl, aryl, substituted aryl aralkyl or substituted aralkyl as defined below.

The term "acyl" denotes groups -C(O)R, where R is alkyl or substituted alkyl, aryl, or substituted aryl as defined below.

The term "aryloxyl" denotes groups -OAr, where Ar is an aryl or substituted aryl group as defined below.

The term "amino" denotes the group NRR', where R and R' may independently be hydrogen, lower alkyl, substituted lower alkyl, aryl, substituted aryl as defined below or acyl.

The term "amido" denotes the group -C(O)NRR', where R and R' may independently be hydrogen, lower alkyl, substituted lower alkyl, aryl, substituted aryl as defined below or acyl.

"Lower alkyl" refers to a cyclic, branched or straight chain, alkyl group of one to eight carbon atoms. This term is further exemplified by such groups as methyl, ethyl, n-propyl, i-propyl, n-butyl, t-butyl, i-butyl (or 2-methylpropyl), cyclopropylmethyl, i-amyl, n-amyl, and hexyl. "Substituted lower alkyl" refers to lower alkyl as just described including one or more functional groups such as lower alkyl, aryl, aralkyl, acyl, halogen, hydroxyl, amino, mercapto and the like. These groups may be attached to any carbon atom of the lower alkyl moiety.

"Aryl" or "Ar" refers to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl). "Substituted aryl" refers to aryl optionally substituted with one or more functional groups, e.g., halogen, lower alkyl, lower alkoxyl, lower alkylthio, trifluoromethyl, lower acyloxyl, hydroxyl and the like.

"Arylene" refers to a doubly substituted aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl). "Substituted arylene" refers to arylene optionally substituted with one or more functional groups, e.g., halogen, lower alkyl, lower alkoxyl, lower alkylthio, trifluoromethyl, lower acyloxyl, hydroxyl and the like.

"Heterocycle" refers to a saturated, unsaturated, or aromatic carbocyclic group having a single ring (e.g., morpholino, pyridyl or furyl) or multiple condensed rings (e.g., naphthyridinyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, lower alkylthio, trifluoromethyl, lower acyloxy, and hydroxy. The term "heteroaryl" or "HetAr" refers to a heterocycle in which at least one heterocyclic ring is aromatic.

"Aralkyl" refers to the group -R-Ar where Ar is an aryl group and R is straight-chain or branched-chain aliphatic group. Aralkyl groups can optionally be unsubstituted or substituted with, e.g., halogen, lower alkyl, lower alkoxy, lower alkylthio, trifluoromethyl, lower acyloxy, and hydroxy.

"Heteroarylalkyl" refers to the group -R-HetAr where HetAr is an heteroaryl group and R is straight-chain or branched-chain aliphatic group. Heteroarylalkyl groups can optionally be unsubstituted or substituted with, e.g., halogen, lower alkyl, lower alkoxyl, lower alkylthio, trifluoromethyl, lower acyloxyl, and hydroxy.

"Akylene" refers herein to a divalent lower alkyl substituent as defined above, such as methylene (-$CH_2$-), ethylene (-$CH_2CH_2$-) or propylene (-$CH_2CH_2CH_2$-).

"Cycloalkylene" refers to a divalent cyclic or polycyclic alkyl group containing 3 to 12 carbon atoms. "Substituted cycloalkylene" refers to a cycloalkylene group comprising one or more substituents, e.g., halogen, lower alkyl, lower alkoxyl, lower alkylthio, trifluoromethyl, lower acyloxy, and hydroxyl.

"Cycloheteroalkylene" refers to a cycloalkylene group wherein one or more of the ring carbon atoms is replaced with a heteroatom (e.g., N, O, S or P). "Substituted cycloheteroalkylene" refers to a cycloheteroalkylene group as herein defined which contains one or more substituents, such as halogen, lower alkyl, lower alkoxyl, lower alkylthio, trifluoromethyl, lower acyloxyl, and hydroxyl.

"Pharmaceutically acceptable salt" refers to those salts which retain the biological effectiveness and properties of the parent compound and which are not biologically or otherwise undesirable.

"Pharmaceutically or therapeutically acceptable carrier" refers to a carrier medium which does not interfere with the effectiveness of the biological activity of the active ingredients and which is not toxic to the host or patient.

"Stereoisomer" refers to a chemical compound having the same molecular weight, chemical composition, and constitution as another, but with the atoms grouped differently. That is, certain identical chemical moieties are at different orientations in space and, therefore, when pure, has the ability to rotate the plane of polarized light. However, some pure stereoisomers may have an optical rotation that is so slight that it is undetectable with present instrumentation. The compounds of the present invention may have one or more asymmetrical carbon atoms and therefore include various stereoisomers. All stereoisomers are included within the scope of the invention.

"Treatment" or "treating" refers to any administration of a tryptase inhibitor in vitro or in vivo and includes:

(i) inhibiting the symptoms of the disease; and/or (ii) lessening or inhibiting the long term effects of the disease.

II. Tryptase Inhibitors

The present invention includes compounds having the general structure:

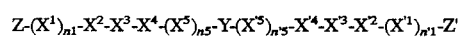

and their pharmaceutically acceptable salts. Y is arylene or substituted arylene. Z and Z' independently are

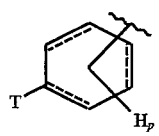

where T is -CH$_2$NH$_2$ or -NHC(NH)NH$_2$; and p is an integer between 0 and 10 inclusive.

X$^1$, X'$^1$, X$^5$ and X'$^5$ are methylene or substituted methylene, and n$_1$, n'$_1$, n$_5$ and n'$_5$ independently are 0 or 1. X$^2$, X'$^2$, X$^4$ and X'$^4$ are selected independently from the group consisting of -NRC(O) , -C(O)NR-, -NRC(O)NR'-, -NRC(O)O- and -OC(O)NR-, wherein R and R' are selected independently from the group consisting of hydrogen, lower alkyl, aryl, substituted lower alkyl, substituted aryl, aralkyl and substituted aralkyl. X$^3$ and X'$^3$ are selected independently from the group consisting of cycloalkylene, cycloheteroalkylene, substituted cycloalkylene, and substituted cycloheteroalkylene, lower alkylene and substituted lower alkylene.

In preferred embodiments, Y is arylene carrying one or more substituents. Typical substituents include halogen, alkoxyl, hydroxyl, alkylthio, carboxyl, mercapto, amido, alkyl, aryl, heteroaryl, aryloxyl, cyano, alkylcarbonyl, arylcarbonyl, alkylimino, arylimino, alkyliminoxyl, aryliminoxyl, nitro, sulfate, sulfonate, phosphate and phosphonate. More preferably, Y is phenylene or phenylene substituted as just described.

Z and Z' independently are

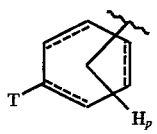

where T is aminomethyl or guanidyl and p is an integer from 0 to 10 inclusive. Thus, Z and Z' independently may include a phenyl, cyclohexadienyl, cyclohexenyl or cyclohexyl ring structure which includes either an aminomethyl or guanidyl group. Preferably, the substituent T is attached to the ring at a carbon meta or para to the carbon at which the ring is attached to the remainder of the molecule. If the ring is phenyl, it may carry one or more substituents such as, but not limited to, halogen, alkoxyl, hydroxyl, alkyl, aryl, heteroaryl, aryloxyl and cyano. Preferred embodiments are those wherein p is 4 or 10, i.e., wherein the ring is phenyl or cyclohexyl. More preferred are those embodiments wherein p is 4 and T is aminomethyl. Still more preferred are those embodiments wherein p is 4 and T is aminomethyl or -NHC(NH)NH$_2$ and attached to the ring at the carbon pars to the carbon atom at which the ring is attached to the molecule.

The compounds of the present invention may include groups X$^1$ and/or X'$^1$, depending on whether the value of n$_1$ and/or n'$_1$ is 0 or 1. When n$_1$ (or n'$_1$) is 0, the group X$^1$ (or X'$^1$) is not a constituent of the molecule, and the Z (or Z') moiety is attached directly to X$^2$ (or X'$^2$). When n$_1$ or n'$_1$ is 1, Z (or Z') is attached to X$^1$ (or X'$^1$). Similarly, when n$_5$ (or n'$_5$) is 0, the group Y is attached directly to X$^4$ (or X'$^4$).

X$^1$, X'$^1$, X$^5$ and X'$^5$ may independently be methylene or substituted methylene. Typical substituents include halogen, alkoxyl, hydroxyl, alkylthio, mercapto, carboxyl, amido, alkyl, aryl, heteroaryl, aryloxyl, cyano, alkylcarbonyl, arylcarbonyl, alkylimino, arylimino, alkyliminoxyl, aryliminoxyl, nitro, sulfate, sulfonate, phosphate and phosphonate. Preferably, X$^1$, X'$^1$, X$^5$ and X'$^5$ are each methylene.

X$^2$, X'$^2$, X$^4$ and X'$^4$ are selected independently from the group consisting of -NRC(O)-, -C(O)NR-, -NRC(O)NR'-, -NRC(O)O- and -OC(O)NR-, wherein R and R' are selected independently from the group consisting of hydrogen, lower alkyl, aryl, substituted lower alkyl, substituted aryl, aralkyl, and substituted aralkyl. It will be appreciated that the groups -NRC(O)- and -NRC(O)O- will define different embodiments depending on their orientation in the molecule. Thus, it will be understood herein that -NRC(O)- refers to an embodiment in which the group to the left of -NRC(O)- (i.e., Z, X$^1$, X$^3$, X'$^3$, X$^5$ or Y) is attached to the nitrogen and the group to the right of -NRC(O)- (i.e., X$^3$, X$^5$, Y, X'$^3$, X'$^1$ or Z') is attached to the carbonyl carbon. Similarly, -C(O)NR- refers to an embodiment which has the group to the left of -C(O)NR- (i.e., Z, X$^1$, X$^3$, X'$^3$, X'$^5$ or Y) attached to the carbonyl carbon and the group to the right of -C(O)NR- (i.e., X$^3$, X$^5$, Y, X'$^3$, X'$^1$ or Z') attached to the nitrogen. The same is to be understood for the case wherein X$^2$ (or X'$^2$, X$^4$ or X'$^4$) is -NRC(O)O- or NRC(O)NR'- (where R and R' have different chemical identities).

X$^3$ and X'$^3$ are selected independently from the group consisting of cycloalkylene, cycloheteroalkylene, substituted cycloalkylene, lower alkylene and substituted lower alkylene. Typical substituents include halogen, alkoxyl, hydroxyl, alkylthio, mercapto, carboxyl, amido, alkyl, aryl, heteroaryl, aryloxyl, cyano, alkylcarbonyl, arylcarbonyl, alkylimino, arylimino, alkyliminoxyl, aryliminoxyl, nitro, sulfate, sulfonate, phosphate and phosphonate. Preferred embodiments are those wherein X$^3$ and X'$^3$ are selected independently from the group consisting of methylene, ethylene and propylene. However, it is also preferred that X$^3$ and X'$^3$ are not methylene when X$^2$ and X$^4$ are both -RNC(O)-, and X'$^4$ and X'$^2$ are both -C(O)NR-, respectively.

Preferred combinations of X$^1$-X$^5$ and X'$^1$-X'$^5$ are shown in Table I below (Ø signifies no group present).

TABLE I

| X$^1$ (X'$^1$) | X$^2$ (X'$^2$) | X$^3$ (X'$^3$) | X$^4$ (X'$^4$) | X$^5$ (X'$^5$) |
|---|---|---|---|---|
| —CH$_2$— | —HNC(O)— | —CH$_2$— | —HNC(O)O— | —CH$_2$— |
| —CH$_2$— | —HNC(O)— | —(CH$_2$)$_2$— | —C(O)NH— | —CH$_2$— |
| —CH$_2$— | —HNC(O)— | —CH$_2$— | —C(O)NR— | —CH$_2$— |
| Ø | —C(O)NH— | —(CH$_2$)$_3$— | —RNC(O)O— | —CH$_2$— |
| —CH$_2$— | —HNC(O)— | —(CH$_2$)$_3$— | —C(O)NH— | —CH$_2$— |
| —CH$_2$— | —HNC(O)— | —(CH$_2$)$_3$— | —HNC(O)— | Ø |
| —CH$_2$— | —HNC(O)— | —(CH$_2$)$_3$— | —C(O)NR— | —CH$_2$— |
| Ø | —C(O)NH— | —(CH$_2$)$_3$— | —C(O)NH— | —CH$_2$— |
| —CH$_2$— | —HNC(O)— | —(CH$_2$)$_2$— | —HNC(O)O— | —CH$_2$— |
| —CH$_2$— | —HNC(O)— | —(CH$_2$)$_3$— | —RNC(O)— | Ø |
| —CH$_2$— | —HNC(O)— | —(CH$_2$)$_2$— | —C(O)NR— | —CH$_2$— |
| —CH$_2$— | —HNC(O)— | —CH$_2$— | —C(O)NH— | —CH$_2$— |

TABLE I-continued

| $X^1$ ($X'^1$) | $X^2$ ($X'^2$) | $X^3$ ($X'^3$) | $X^4$ ($X'^4$) | $X^5$ ($X'^5$) |
|---|---|---|---|---|
| ∅ | —C(O)NH— | —(CH$_2$)$_4$— | —HNC(O)— | ∅ |
| ∅ | —C(O)NH— | —(CH$_2$)$_2$— | —HNC(O)O— | —CH$_2$— |
| —CH$_2$— | —HNC(O)— | | —C(O)NH— | —CH$_2$— |
| —CH$_2$— | —HNC(O)— | —(CH$_2$)$_2$— | —C(O)NH— | —CH(CO$_2$H)— |

Generally, the compounds of the invention are synthesized using standard techniques and reagents. It will be noted that the linkages between the various groups, Z, Z', $X^1$-$X^5$ and $X'^1$-$X'^5$, comprise carbon linked to the nitrogen of an amide or carbamate, the oxygen of a carbamate or the carbon of a carbonyl. Those of skill in the art will recognize that methods and reagents for forming these bond are well known and readily available. See, e.g., March, ADVANCED ORGANIC CHEMISTRY, 4th Ed. (Wiley 1992), Larock, COMPREHENSIVE ORGANIC TRANSFORMATIONS (VCH 1989); and Furniss, et al. and Furniss, VOGEL'S TEXTBOOK OF PRACTICAL ORGANIC CHEMISTRY 5th ed. (Longman 1989), each of which is incorporated herein by reference. It will also be appreciated that any functional groups present may require protection and deprotection at different points in the synthesis of the compounds of the invention. Those of skill in the art will also recognize that such techniques are well known (see, e.g., Green and Wuts, PROTECTIVE GROUPS IN ORGANIC CHEMISTRY (Wiley 1992), also incorporated herein by reference).

The various groups Z, Z', $X^1$-$X^5$ and $X'^1$-$X'^5$ which comprise the target molecule to be synthesized may be added individually, or as larger chemical subunits which together form the desired molecule. Thus, for example, where it is desired that $X^5$ and $X'^5$ are -CH$_2$-, Y is phenylene, and $X^4$ and $X'^4$ are -NHC(O)O- or -HNC(O)NH-, p-diaminoxylylene (H$_2$NCH$_2$-C$_6$H$_4$-CH$_2$NH$_2$) may be used to supply the Y, $X^5$ and $X'^5$ groups as well as a nitrogen of the $X^4$ and $X'^4$ groups. Similarly, where Y and $X^5$ and $X'^5$ are defined as above, and $X^4$ and $X'^4$ are -OC(O)NH-, dihydroxyxylylene may be used. Reaction of this unit with phosgene, followed by reaction with a group such as N-BocZ-$X^1$-$X^2$-$X^3$-OH or N-BocZ-$X^1$-$X^2$-$X^3$-NH$_2$ under standard conditions, forms the corresponding symmetrical molecules as illustrated below. Those of skill in the art will appreciate that other equivalent synthetic pathways are possible.

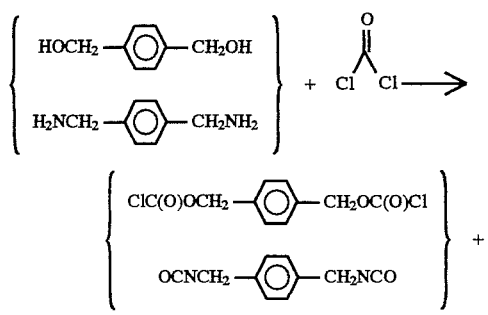

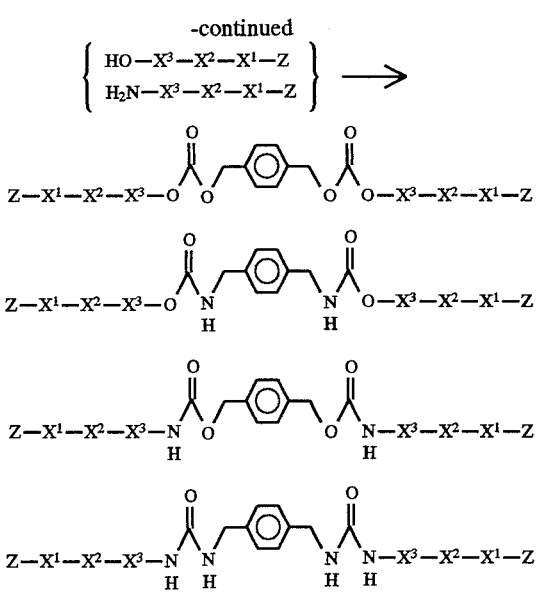

Similar methodologies to those just described are employed for cases where Y is arylene other than phenylene or substituted arylene, e.g., Y is 1,4-naphthyl, 2-bromophenyl, or 3-methyl-2,6-naphthyl. For those cases where $X^5$ and $X'^5$ are not included, i.e., n$_5$ and n'$_5$ are both 0, p-dihydroxybenzene or p-diaminobenzene may be used instead of dihydroxy- or diaminoxylylene. The synthesis may be performed by analogy to the steps outlined above.

The synthesis of asymmetric compounds may be accomplished using the techniques described in conjunction with appropriate starting materials and/or appropriate selective protection and deprotection strategies. For example, where either n$_5$ or n'$_5$ is 0, but the remainder of the molecule is symmetric, the strategy just discussed may be employed using 4-hydroxybenzyl alcohol or 4-aminobenzylamine.

Alternatively, compounds having functional groups with different reactivities may be chosen. Following reaction at a desired first functional group, a second functional group may be converted to a more reactive form. For example, as shown below, 4-nitroaniline or 4-nitrobenzylamine may be used to form an amide selectively at one side of Y using standard synthetic techniques as just described, as the nitro group is unreactive towards acylation. ($R^1$ and $R^2$ represent Z-$X^1$-$X^2$-$X^3$ and Z'-$X'^1$-$X'^2$-$X'^3$ respectively.) Reduction of the resulting 4-nitrophenylamide or 4-nitrobenzylamide to form the corresponding 4-amino derivative imparts reactivity to the other side of Y with respect to acylation with a different acyl derivative using the methods described above.

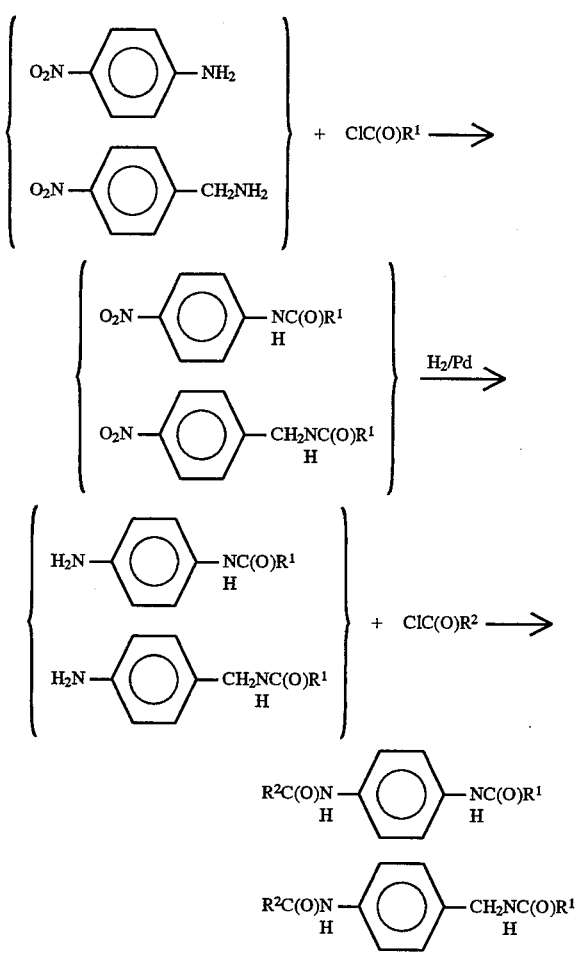

This strategy may also be followed in cases where it is desired to combine a carbamate group on one side of Y, e.g., Y-OC(O)NHR, with an amide, -C(O)NH-, carbamate, -HNC(O)OR, or urea, -HNC(O)NRR' attached at the other side of Y (R and R' are hydrogen, $Z-X^1-X^2-X^3$ or $Z'-X'^1-X'^2-X'^3$). For example, 4-nitrophenol, 4-nitrobenzyl alcohol, or 4-nitromethylphenol may be employed in place of the aromatic groups just described to form the corresponding acylated compounds by first reacting the alcohol moiety with the first acyl group at one side of the desired molecule, followed by reduction of the nitro group to form the corresponding amine and reacting the amine with the second acyl group to complete the molecule.

Those of skill in the art will also appreciate that the units $-X^1-X^2-X^3-X^4-$ and $-X'^1-X'^2-X'^3-X'^4-$, and their various subunits, may be formed by techniques known in the art and by analogy to the examples provided herein. It will also be appreciated that amino acids provide convenient building blocks from which to create the various functionalities which comprise the elements $X^1-X^4$ and $X'^1-X'^4$. The amino acids used herein include the twenty naturally occurring L-amino acids and their D- isomers as well as their derivatives. Amino acid derivatives include compounds such as norvaline, hydroxyproline, N-methyl-L-leucine, aminoisobutyric acid, statine, γ-carboxyglutamic acid, serine-O-phosphate, tyrosine-O-phosphate, tyrosine-O-sulfate, pyroglutamic acid and 4-(E)-butenyl-4-(R)-methyl-N-methyl-L-threonine. Other amino acid derivatives include the natural amino acids in which side chain functionality is derivatized or protected with common protecting groups, e.g., t-butoxycarbonyl (BOC). The techniques and methods used to synthesize, purify and evaluate such compounds are well known in the art and are described, e.g., in SYNTHETIC PEPTIDES: A USER'S GUIDE, Grant, Ed., (Freeman 1992); and SOLID PHASE PEPTIDE SYNTHESIS: A PRACTICAL APPROACH, Atherton, et al., Eds. (IRL Press 1989), both of which are incorporated herein by reference.

In some cases $X^3$ or $X'^3$ will be cycloheteroalkylene, e.g., pyrrolidine, piperidine, piperazine, as well as cyclic ethers, ketals, acetals and orthoesters. These groups may be added as individual units or formed in situ from appropriately substituted alkylenes using standard methods, such as those described in Green and Wuts or March, supra.

The groups Z and Z' are formed readily using standard starting materials and commonly known synthetic techniques. Generally, the considerations discussed above with respect to the formation of the linkages between Y, $X^5$ ($X'^5$) and $X^4$ ($X'^4$) apply equally well to the linkages between Z (Z'), $X^1$ ($X'^1$) and $X^2$ ($X'^2$). For example, if $X^1$ ($X'^1$) is methyl and $X^2$ ($X'^2$) includes a nitrogen linkage to $X^1$ ($X'^1$), then p-xylylenediamine may be chosen as a starting material. One of the two aminomethyl groups may be protected as the N-butoxycarbonyl (BOC) derivative using a stoichiometric excess of p-xylylenediamine and following standard procedures (Green and Wuts, supra). The free amino group may then be reacted with an acyl derivative to form the $Z-X^1$-NC(O)- portion of the molecule. The same strategy just described is applicable to the cases where Z includes a cyclohexadienyl, cyclohexenyl or cyclohexyl ring system.

Similar methodology is applied where $X^2$ is a carbamate (-OC(O)NR-). For example, starting from the N-BOC-protected p-xylylenediamine discussed above, reaction with $N_2O_4$ followed by reaction with Zn and acetic acid converts the free amine to an alcohol (Larock, supra; JCS Perkin I, 1114 (1977), which is incorporated herein by reference). The alcohol is reacted with an acyl derivative to give the desired product. The same strategy just described is applicable to the cases where Z includes a cyclohexadienyl, cyclohexenyl or cyclohexyl ring system.

For cases where $n_1$ ($n'_1$) is 0, the strategies discussed above may be followed using starting materials such as 4-nitrobenzylamine, 4-hydroxybenzylamine or 4-aminomethylbenzoyl chloride. These reagents are commercially available, (e.g., from Aldrich Chemical Co., Milwaukee, Wis.) or can be synthesized using known techniques. Protection of the amine (for example, as the N-BOC derivative), is followed by conversion of nitro group to a free amine and/or reaction with an amine, alcohol or activated acyl group to attach the Z or Z' group to the $X^2$ ($X'^2$) substituent. The same strategy just described is applicable to the cases where Z includes a cyclohexadienyl, cyclohexenyl or cyclohexyl ring system.

The guanidyl-substituted variants are formed by analogy to the methods described hereinabove. However, the aminomethyl substituent is replaced by an amino substituent which is converted to the guanidyl moiety using standard techniques such as, for example, reaction of the amine with cyanamide.

Those of skill in the art will also appreciate that the compounds of the present invention may be derived from other compounds of the invention using well-known chemical transformations.

Compounds of this invention can, depending on the nature of their functional groups, form addition salts with various inorganic and organic acids and bases. Typical inorganic acids include, e.g., hydrochloric acid, hydrobromic acid, sulfuric acid, nitric acid, phosphoric acid and the like. Typical organic acids include, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Salts can also be formed from a carboxylic acid residue by treatment with alkali metals or alkali metal bases, such as alkali metal hydroxides and alkali metal alkoxides, or alkaline earth metals or alkaline earth metal bases, such as alkaline earth metal hydroxides and alkaline earth metal alkoxides. In addition, salts can be formed from a carboxylic acid and an organic base, such as trimethylamine, diethylamine, ethanolamine, piperidine, isopropylamine, choline, caffeine, and the like.

The salts can be formed by conventional means, as by reacting the free acid or base forms of the product with one or more equivalents of the appropriate base or acid in a solvent or medium in which the salt is insoluble, or in a solvent such as water, which is then removed in vacuo or by freeze-drying or by exchanging the cations of an existing salt for another cation on a suitable ion exchange resin.

III. In Vitro and In Vivo Testing

In vitro protocols for screening potential inhibitors as to their ability to inhibit tryptase are known in the art. See, e.g., Sturzebecher et al. (1992) *Biol. Chem. Hoppe-Seyler* 373:1025-1030. Typically, these assays measure the tryptase-induced hydrolysis of peptide-based chromogenic substances. Details of an exemplary procedure are described below.

In addition, the activity of the compounds of the present invention can be evaluated in vivo in one of the numerous animal models of asthma. See Larson, "Experimental Models of Reversible Airway Obstruction", in THE LUNG: SCIENTIFIC FOUNDATIONS, Crystal, West et al., eds., Raven Press, New York, 1991; Warner et al. (1990) *Am. Rev. Respir. Dis.* 141:253-257. An ideal animal model would duplicate the chief clinical and physiological features of human asthma, including: airway hyperresponsiveness to chemical mediators and physical stimuli; reversal of airway obstruction by drugs useful in human asthma ($\beta$-adrenergics, methylxanthines, corticosteroids, and the like); airway inflammation with infiltration of activated leukocytes; and chronic inflammatory degenerative changes, such as basement membrane thickening, smooth muscle hypertrophy, and epithelial damage. Species used as animal models include mice, rats, guinea pigs, rabbits, dogs, and sheep. All have some limitations, and the proper choice of animal model depends upon the question which is to be addressed.

The initial asthmatic response can be evaluated in guinea pigs, and dogs, and particularly, with a basenji-greyhound cross strain which develops nonspecific airway hyperresponsiveness to numerous nonallergenic substances, such as methacholine and citric acid. Certain selected sheep exhibit a dual response after antigen challenge with Ascaris proteins. In dual responding animals, the initial asthmatic response (IAR) is followed by a late asthmatic response (LAR) at 6-8 hours post-exposure. Hypersensitivity to the cholinergic agonist carbachol increases at 24 hours after antigen challenge in those animals which exhibit LAR.

The allergic sheep model (see below) was used to evaluate the potential antiasthmatic effects of the compounds of the present invention. Administration of compositions comprising aerosolized solutions of the compounds of the present invention to allergic sheep prior to or following exposure to specific allergens demonstrates that such compositions substantially lessen or abolish the late asthmatic response and consequent hyperresponsiveness.

The compounds of this invention are also useful for the treatment of other immunomediated inflammatory disorders in which tryptase activity contributes to the pathological condition. Such diseases include inflammatory diseases associated with mast cells, such as rheumatoid arthritis, conjunctivitis, rheumatoid spondylitis, osteoarthritis, gouty arthritis and other arthritic conditions, inflammatory bowel disease, peptic ulcers and various skin conditions.

The efficacy of the compounds of the present invention for the treatment of the vast majority of immunomediated inflammatory disorders can be evaluated by either in vitro or in vivo procedures. Thus, the anti-inflammatory efficacy of the compounds of the present invention can be demonstrated by assays well known in the art, for example, the Reversed Passive Artbus Reaction (RPAR)-PAW technique (see, e.g., Gangly et al. (1992) U.S. Pat. No. 5,126,352). Assays for determining the therapeutic value of compounds in the treatment of various skin conditions, such as hyperproliferative skin disease, are well known in the art, for example, the Arachidonic Acid Mouse Ear Test (Id.). The compounds of the present invention can be evaluated for their antiulcer activity according to the procedures described in Chiu et al. (1984) *Archives Internationales de Pharmacodynamie et de Therapie* 270:128-140.

IV. In Vivo Administration

According to this invention, a therapeutically or pharmaceutically effective amount of a compound of the invention is administered to a patient suffering from an immunomediated inflammatory disorder. According to one embodiment, the compositions of the present invention are useful for preventing or ameliorating asthma. In using the compositions of the present invention in a treatment of asthma, the compounds may be administered prophylactically prior to exposure to allergen or other precipitating factor, or after such exposure. The compounds of the present invention are particularly useful in ameliorating the late-phase tissue destruction seen in both seasonal and perennial rhinitis. Another aspect of the present invention is directed to the prevention and treatment of other immunomediated inflammatory disorders associated with mast cells such as urticaria and angioedema, and eczematous dermatitis (atopic dermatitis), and anaphylaxis, as well as hyperproliferative skin disease, peptic ulcers, and the like.

The compositions containing the compounds can be administered for therapeutic and/or prophylactic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective amount or dose." Amounts effective for this use will depend on the severity and course of the disease, previous therapy, the patient's health status and response to the drugs, and the judgment of the treating physician.

In prophylactic applications, compositions containing the compounds of the invention are administered to a patient susceptible to or otherwise at risk of a particular disease in an amount sufficient to prevent or ameliorate the onset of symptoms. Such an amount is defined to be a "prophylactically effective amount or dose." These can be administered orally or by inhalation. In this use, the precise amounts again depend on the patient's state of health, weight, and the like.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

In general, a suitable effective dose of the tryptase inhibitor will be in the range of 0.1 to 1000 milligram (mg) per recipient per day, preferably in the range of 1 to 100 mg per day. The desired dosage is preferably presented in one, two, three, four or more subdoses administered at appropriate intervals throughout the day. These subdoses can be administered as unit dosage forms, for example, containing 5 to 1000 mg, preferably 10 to 100 mg of active ingredient per unit dosage form.

The composition used in these therapies can be in a variety of forms. These include, for example, solid, semi-solid and liquid dosage forms, such as tablets, pills, powders, liquid solutions or suspensions, liposomes, injectable and infusible solutions. Inhalable preparations, such as aerosols, are also included. Preferred formulations are those directed to oral, intranasal and topical applications, but it will be appreciated that the preferred form will depend on the particular therapeutic application at hand. The methods for the formulation and preparation of therapeutic compositions comprising the compounds of the invention are well known in the art and are described in, for example, REMINGTON'S PHARMACEUTICAL SCIENCES and THE MERCK INDEX 11$^{th}$ Ed., (Merck & Co. 1989).

While it is possible to administer the active ingredient of this invention alone, it is preferable to present it as part of a pharmaceutical formulation. The formulations of the present invention comprise at least one compound or inhibitor described herein in a therapeutically or pharmaceutically effective dose together with a pharmacologically acceptable carrier. The formulation may include other clinically useful compounds, such as β-adrenergics (e.g., albuterol, terbutaline, formoterol, fenoterol, and prenaline) and corticosteroids (e.g., beclomethasome, triamcinolone, flurisolide, and dexamethasone).

EXAMPLES

The following examples are provided merely for the purposes of illustration and are not to be construed in any way as limiting the scope of the present invention.

General Materials and Methods

The compounds described herein may be formed using techniques which are well known in the art, such as those techniques described in March, ADVANCED ORGANIC CHEMISTRY (Wiley 1992); Larock, COMPREHENSIVE ORGANIC TRANSFORMATIONS (VCH 1989); and Furniss, et al., VOGEL'S TEXTBOOK OF PRACTICAL ORGANIC CHEMISTRY 5th ed. (Longman 1989), each of which is incorporated herein by reference. It will be appreciated that the syntheses described herein may require one or more protection and deprotection steps. Accordingly, the use of appropriate protecting groups is necessarily implied by the processes contained herein, although not expressly illustrated. Such protection and deprotection steps may be accomplished by standard methods in addition to those described herein, such as those described in Green and Wuts, PROTECTIVE GROUPS IN ORGANIC SYNTHESIS (Wiley 1991), which is incorporated herein by reference.

Isolation and purification of the compounds and intermediates described herein can be effected, if desired, by any suitable separation or purification procedure such as, for example, filtration, extraction, crystallization, column chromatography, thin-layer chromatography or thick-layer chromatography, high-pressure liquid chromatography (HPLC), or a combination of these procedures. Specific illustrations of suitable separation and isolation procedures can be had by reference to the examples hereinbelow. However, other equivalent separation or isolation procedures can, of course, be used.

Nuclear magnetic resonance (NMR) spectra were recorded on a General Electric "QE Plus" spectrometer (300 MHz). Infrared (IR) spectra were recorded on a Perkin-Elmer 1600 Fourier Transform IR (FTIR). Analytical HPLC was performed on a Ultrafast Microprotein Analyzer, Michrom BioResources, Inc. equipped with a PLRP column, 1 mm×150 mm. Preparative HPLC was performed on a Gilson LC using a VYDAC 1×25 cm $C_{18}$ reverse phase (RP) column or a Waters Prep LC2000 system using a Vydac 5×25 cm $C_{18}$ RP column. Mass spectra (MS) were obtained on a Finnigan SSQ 710 with an ESI source by direct infusion or by HPLC MS (Ultrafast Microprotein Analyzer, $C_{18}$ column 2 mm×150 mm).

Unless otherwise noted, all reagents and equipment were either prepared according to published procedures or were purchased from commercial sources, such as Aldrich Chemical Co. (Milwaukee, Wis.), Sigma Chemical Co. (St. Louis, Mo.) and ICN Chemical Co. (Irvine, Calif.). The techniques used to perform the syntheses described below will be recognized by those of skill in the art as routine (see, e.g., March, Larock, or Furniss supra).

EXAMPLE 1

Bis(p-xylylenediamineglycine)-1,4-benzenedimethanol dicarbamate

Reagents and solvents were used as received from the commercial suppliers, except for dioxane which was passed through a column of basic alumina using flash chromatography techniques before use.

A solution containing 10 milliliters (mL) di-tert-butyl dicarbonate (0.044 moles (mol), 1.0 equivalents (equiv)) in dioxane (100 mL) was added dropwise to a solution of 47 grams (g) p-xylylenediamine (0.35 mol, 8.0 equiv) in dioxane (300 mL) over a period of 7 h. The resulting white suspension was stirred at 23° C. for 14 h and concentrated. The residue was partitioned between ethyl acetate (three portions), water (four portions), and saturated aqueous sodium chloride. The organic layer was dried over magnesium sulfate and concentrated, providing crude N-Boc-p-xylylenediamine (9.69 g) as a pale yellow solid.

To a solution of 1.0 g N-Boc-p-xylylenediamine (4.23 mmol, 1.0 equiv) in N,N,-dimethylformamide (25 mL) was added 0.63 g 1-hydroxybenzotriazole hydrate (4.65 mmol, 1.1 equiv), 0.88 g N-Cbz-glycine (4.23 mmol, 1.0 equiv), and 0.58 mL 4-methylmorpholine (5.29 mmol, 1.25 equiv). 1-(3-Dimethylaminopropyl)-3-ethylcarbodiimide hydrochloride (0.89 g, 4.65 mmol, 1.1 equiv) was added to the reaction mixture at 0° C. The yellow solution was stirred at 0° C. for 1 h and at 23° C. for 19 h. The reaction mixture was partitioned between dichloromethane, saturated aqueous sodium bicarbonate, 0.05N hydrochloric acid, and saturated aqueous sodium chloride. The organic layer was dried over sodium sulfate, and concentrated to give crude N-CBZ-glycine-p-xylylenediamine-N-Cbz as a yellow solid.

Ethanol (50 mL) was added to a vessel holding 1.0 g of the N-Boc-p-xylylenediamine-glycine-N-Cbz (2.34 mmol, 1.0 equiv) and palladium on activated carbon (5%, 2.5 g, 2.5 wt equiv) under a nitrogen atmosphere. The black suspension was swept with hydrogen, and stirred under 1 atmosphere (atm) of hydrogen for 4 h. The reaction mixture was then swept with nitrogen and filtered through celite. The celite pad was washed with ethanol, dichloromethane, and 10% methanol in dichloromethane. Crude glycine-p-xylylenediamine-N-BOC was obtained as a yellow oil.

A 1.93 molar (M) solution of phosgene in toluene (50 mL, 0.097 mol, 2.7 equiv) was added to 5.0 g 1,4-benzenedimethanol (0.036 mol, 1.0 equiv) at 0° C. The reaction mixture was stirred for 19.5 hours (h), during which time the ice bath was allowed to melt, resulting in a final reaction temperature of 23° C. Nitrogen was bubbled through the yellow solution for 25 min. The solution was concentrated, giving crude 1,4-benzenedimethanol dichloroformate (8.32 g) as a yellow oil.

A solution of 0.020 mL 1,4-benzenedimethanol dichloroformate (0.12 mmol, 1.0 equiv) and pyridine (0.030 mL, 0.36 mmol, 3.0 equiv) was added to a solution of 90 mg N-Boc-p-xylylenediamine-glycine-NH$_2$ (0.30 mmol, 2.5 equiv) in dichloromethane (3 mL). The white suspension was stirred at 23° C. for 19 h. The reaction mixture was partitioned between dichloromethane, 0.05N hydrochloric acid, saturated aqueous sodium bicarbonate, and saturated aqueous sodium chloride. The organic layer was dried over sodium sulfate and concentrated to give crude bis(N-Boc-p-xylylenediamine-glycine)-1,4-benzenedimethanol-dicarbamate as a white residue.

The bis(N-Boc-p-xylylenediamineglycine)-1,4-benzenedimethanol dicarbamate obtained was stirred in 50% trifluoroacetic acid in dichloromethane (4 mL) at 23° C. for 35 min. The reaction mixture was concentrated. The residue was concentrated with ether, and the solid obtained rinsed with ether (two portions) and further purified by preparative scale liquid chromatography, to give bis(p-xylylenediammonium-glycine)-1,4-benzenedimethanol-dicarbamate bis-trifluoroacetate.

Analysis: $^1$H NMR (300 MHz, CD$_3$OD): 7.40 (s, 12 H), 5.10 (s, 4 H), 4.40 (d, 4 H), 4.05 (s, 4 H), 3.80 (s, 4 H). Mass Spectrum: (calcd) for C$_{30}$H$_{36}$N$_6$O$_6$ (M+): 578, found: 578.

EXAMPLE 2

1,4-Benzenedimethanol bischloroformate ("bischloroformate")

1,4-benzenedimethanol (1.0 g, 7.2 mmol) was slowly added to 10 mL of a 1.9M solution of phosgene in toluene at 0° C. over several minutes. The mixture was allowed to slowly warm to room temperature with stirring under a nitrogen atmosphere for an additional twelve hours. Subsequent removal of toluene in vacuo at room temperature provided the corresponding bischloroformate (1.7 g, 90% yield) as a colorless oil which was employed without further purification.

Analysis. $^1$H-NMR (CDCl$_3$): 7.42 (s, 4H), 5.31 (s, 4H).

1,4-Benzenedimethanol dicarbamate-N,N'-acetic acid

Glycine (12.0 g, 160 mmol) was dissolved in water (100 mL) followed by the addition of sodium hydroxide (5.0 g, 125 mmol) and sodium hydrogen carbonate (5.0 g, 60 mmol). 1,4-benzenedimethanol bischloroformate (8.3 g, 31.5 mmol) was subsequently added to the aqueous solution and the mixture was allowed to stir at room temperature over twelve hours. An additional volume of water (50 mL) was added to the reaction mixture and the diluted solution filtered to remove traces of insoluble residue. The aqueous solution was acidified to a pH of 1 by dropwise addition of concentrated aqueous hydrochloric acid, and the precipitated diacid was collected by filtration. Subsequent washing with water (3×100 mL) and drying in vacuo provided pure biscarbamate as a colorless solid (9.5 g, 89% yield).

Analysis. $^1$H-NMR (DMSO-d$_6$): 7.52 (tr, 2H), 7.31 (s, 4H), 5.02 (s, 4H), 3.65 (d, 4H).

N,N'-(4-Aminobenzylaminecarbonylmethylene)-1,4-benzenedimethanol dicarbamate 9.5 g of 1,4-benzenedimethanol dicarbamate-N,N'-acetic acid (27.9 mmol), 7.95 g hydroxybenzotriazole hydrate (58.8 mmol), and 13.3 mL 4-aminobenzylamine (117.2 mmol) were dissolved in 30 mL of dimethylformamide (DMF), and the resulting yellow solution cooled to 0° C. 1-(3-Dimethylaminopropyl)-3-ethylcarbodiimide hydrochloride (11.2 g, 58.4 mmol) was then added to the mixture which was then allowed to warm slowly to room temperature over twelve hours. Removal of the DMF in vacuo followed by the addition of water (750 mL) and filtration of the insoluble residue gave crude N,N'-(4-aminobenzylaminecarbonylmethylene)-1,4-benzenedimethanol dicarbamate as a waxy white solid. The crude material was then taken into boiling methanol (500 mL) and the resulting suspension cooled to 0° C. Filtration and drying in vacuo provided the desired product (8.0 g, 52% yield) as a colorless solid.

Analysis. $^1$H-NMR (DMSO-d$_6$): 8.10 (tr, 2H), 7.40 (tr, 2H), 7.30 (s, 4H), 6.85 (d, 4H), 6.45 (d, 4H), 5.00 (s, 4H), 4.95 (br s, 4H), 4.15 (d, 4H), 3.60 (d, 4H).

N,N'-(4-Guanidylbenzylaminecarbonylmethylene)-1,4-benzenedimethanol dicarbamate

N,N'-(4-aminobenzylaminecarbonylmethylene)-1,4-benzenedimethanol dicarbamate (100 mg, 0.18 mmol) and cyanamide (1.0 g, 23.8 mmol) were heated neat at 60° C. to give a slurry. This was followed by the addition of 180 μL of a solution of hydrogen chloride in dioxane (4M, 0.7 millimoles (mmol)). The resulting yellow liquid was stirred at 60° C. for an additional 30 minutes followed by cooling to room temperature. Addition of ethyl ether (15 mL) gave an insoluble yellow oil which was repeatedly washed with additional ethyl ether (3×15 mL) to remove residual cyanamide followed by drying in vacuo. The yellow oil was then taken into water (5 mL) and purified by preparative reverse phase HPLC to give N,N'-(4-guanidylbenzylaminecarbonylmethylene) -1,4-benzenedimethanol dicarbamate bis-trifluoroacetate (50 mg, 32% yield) as a colorless solid.

Analysis. $^1$H- NMR (DMSO-d$_6$): 9.80 (s, 2H), 8.45 (tr, 2H), 7.50 (tr, 2H), 7.45 (s, 8H), 7.35 (s, 4H), 7.30 (d, 4H), 7.20 (d, 4H), 5.05 (s, 4H), 4.30 (d, 4H), 3.65 (d, 4H). Electrospray LRMS: Calculated for C$_{30}$H$_{36}$N$_{10}$O$_6$: MH$^+$: 633.7; MH$_2^{+2}$/2: 317.4. Found: MH$^+$: 633.4; MH$_2^{+2}$2: 317.2

Another synthesis of EXAMPLE 2.

To a solution of 1,4-benzenedimethanol (1.40 g, 10.1 mmol) in dimethylformamide (50 mL) was added copper (I) chloride (300 mg, 3.0 mmol) followed by ethyl isocyanatoacetate (2.76 g, 21.4 mmol) and the resulting suspension was allowed to stir at room temperature over twelve hours.

Water (200 mL) and dichloromethane (200 mL) were added to the mixture and the aqueous phase extracted with additional dichloromethane (200 mL). The combined organic layers were washed with water (2×200 mL) followed by saturated aqueous sodium chloride and dried over anhydrous magnesium sulfate. Filtration followed by concentration and drying in vacuo gave 1,4-benzene-dimethanol-dicarbamate-N,N'-acetic acid bis-ethyl ester (3.83 g, 96%) as a colorless solid. $^1$H-NMR (CDCl$_3$): 7.40 (s, 4H), 5.30 (br s, 2H), 5.15 (s, 4H), 4.25 (q, 4H), 4.00 (d,4H), 1.30 (tr, 6H).

To a solution of 1,4-benzenedimethanol-dicarbamate-N, N'-acetic acid bis-ethyl ester (2.87 g, 7.25 mmol) in tetrahydrofuran:methanol:water 3:1:1 (125 mL) was added sodium hydroxide (1.0 g, 25 mmol) in water (25 mL) and the mixture was allowed to stir at room temperature over four hours. Concentration followed by acidification of the aqueous solution to pH=1 by dropwise addition of concentrated aqueous hydrochloric acid gave a white precipitate. Filtration and drying in vacuo gave 1,4-benzenedimethanoldicarbamate-N,N'-acetic acid as a colorless solid. $^1$H-NMR (DMSO-d$_6$): 7.52 (tr, 2H), 7.31 (s, 4H), 5.02 (s, 4H), 3.65 (d, 4H).

4-Aminobenzylamine (11.0 g, 90 mmol) in dichloromethane (30 mL) was cooled to 0° C. and di-tert-butyl dicarbonate (18.65 g, 85 mmol) was added to the solution and the mixture was allowed to slowly warm to room temperature over twelve hours. Subsequent filtration followed by washing the dichloromethane solution with saturated aqueous ammonium chloride then with saturated aqueous sodium chloride, drying over anhydrous magnesium sulfate, filtration and concentration gave 4-amino-N-tert-butylcarbomoylbenzylamine as a yellow oil. A methanol solution of the aniline was acidified with hydrogen chloride in dioxane (one equivalent) and the hydrochloride salt crystallized by addition of ethyl ether to the acidic solution. Filtration and drying in vacuo provided the hydrochloride salt as a yellow crystalline solid which was guanylated without further purification.

4-Amino-N-tert-butylcarbamoylbenzylamine hydrochloride (25.77 g, 99.6 mmol) and cyanamide (55 g, 1.3 mmol) were heated neat at 65° C. over 1.5 hours. The mixture was then cooled to room temperature and ether (250 mL) was added. The insoluble yellow oil was repeatedly washed with additional ethyl ether to remove traces of cyanamide and dried in vacuo to give 4-guanidyl-N-tert-butylcarbamoylbenzylamine hydrochloride as an amorphous yellow material which was carried on without further purification.

4-Guanidyl-N-tert-butylcarbamoylbenzylamine hydrochloride (14.4 g, 48 mmol) was taken up into trifluoroacetic acid (35 mL) and the resulting yellow solution stirred over 30 minutes. Concentration and drying in vacuo gave 4-guanidyl-benzylamine bis-trifluoroacetate as a yellow oil. $^1$H-NMR (DMSO-d$_6$): 10.25 (s, 1H), 8.40 (br s, 3H), 7.65 (br s, 4H), 7.50 (d, 2H), 7.25 (d, 2H), 4.00 (d, 2H).

1,4-Benzenedimethanol-dicarbamate-N-N'-acetic acid (5.4 g, 15.9 mmol) in dimethylformamide (30 mL) was cooled to 0° C. and hydroxybenzotriazole hydrate (4.6 g, 34.0 mmol) was added followed by 1-(3-Dimethylaminopropyl)-3-ethyl-carbodiimide hydrochloride (6.6 g, 34.3 mmol). The resulting mixture was stirred at 0° C. over one hour then added by cannula to a slurry containing 4-guanidyl-benzylamine bis-trifluoroacetate (14.4 g, 48 mmol) and triethylamine (16.7 g, 165 mmol) in dimethylformamide (20 mL) cooled to 0° C. The mixture was then allowed to slowly warm to room temperature over twelve hours followed by concentration in vacuo. The residue was taken into water (40 mL) and the solution pH adjusted to 11–12 by dropwise addition of saturated aqueous sodium carbonate. The white precipitate was collected by filtration and the solid product taken back into aqueous solution by acidification to pH=1–2 with concentrated aqueous hydrochloric acid. Repetition of this process once followed by careful filtration of the aqueous bis-guanidine hydrochloride using Millipore filter paper type GV (0.22 μm) and lyophilization gave the title compound, N,N'-(4-Guanidylbenzylamine-carbonylmethylene)-1,4-benzenedimethanol dicarbamate bis-hydrochloride, as a colorless solid.

EXAMPLE 3

N,N'-(2-Carboxyethylene)-1,4-benzenedimethanol dicarbamate

β-alanine (512 mg, 5.8 mmol) was dissolved in 3M aqueous sodium hydroxide (3.8 mL) and the resulting solution cooled in an ice bath. 1,4-Benzenedimethanol bischlorformate (756 mg, 2.8 mmol) was added to the aqueous solution followed by an additional 3.8 mL of 3M aqueous sodium hydroxide, and the mixture was allowed to warm slowly to room temperature over twelve hours. The aqueous solution was then acidified to a pH of 1 by dropwise addition of concentrated aqueous hydrochloric acid and the precipitated diacid was collected by filtration. Subsequent washing with water (3×20 mL) and drying in vacuo provided pure N,N'-(2-carboxyethylene)-1,4-benzene-dimethanol dicarbamate as a colorless solid.

Analysis. $^1$H-NMR (DMSO-d$_6$): 12.20 (br s, 2H), 7.35 (s, 4H),7.30 (tr, 2H), 5.00 (s, 4H), 320 (q, 4H), 2.40 (tr, 4H).

N,N'-(4-Aminobenzylaminecarbonylethylene)-1,4-benzenedimethanol dicarbamate

N,N'-(2-carboxyethylene)-1,4-benzenedimethanol dicarbamate (163 mg, 0.44 mmol), hydroxybenztriazole hydrate (132 mg, 0.97 mmol), and 4-aminobenzylamine (238 mg, 1.94 mmol) were dissolved in DMF (1.5 mL) and the resulting yellow solution cooled to 0° C. 1-(3-Dimethylaminopropyl)-3-ethyl-carbodiimide hydrochloride (187 mg, 0.97 mmol) was then added to the mixture and allowed to slowly warm to room temperature over twelve hours. Removal of DMF in vacuo followed by addition of water (25 mL) and filtration of the insoluble residue gave N,N'-(4-aminobenzylaminecarbonylethylene)-1,4-benzenedimethanol dicarbamate (155 mg) as a white solid which was employed without further purification.

Analysis. $^1$H-NMR (DMSO-d$_6$): 8.20 (tr, 2H), 7.35 (s, 4H), 7.25 (tr, 2H), 6.90 (d, 4H), 6.50 (d, 4H), 5.00 (s, 4H), 4.95 (br s, 4H), 4.05 (d, 4H), 3.20 (q, 4H), 2.30 (tr, 4H).

N,N'-(4-Aminobenzylaminecarbonylethylene)-1,4-benzenedimethanol dicarbamate

N,N'-(4-aminobenzylaminecarbonylethylene)-1,4-benzenedimethanol dicarbamate (155 mg, 0.27 mmol) and cyanamide (1.2 g, 28.6 mmol) were heated neat at 60° C. to give a slurry followed by addition of hydrogen chloride (4M in dioxane, 260 μL, 1.1 mmol). The resulting yellow liquid was stirred at 60° C. an additional 1.5 hours followed by cooling to room temperature. Addition of ethyl ether (15 mL) gave an insoluble yellow oil which was repeatedly washed with additional ethyl ether (3×15 mL) to remove residual cyanamide followed by drying in vacuo. The yellow oil was then taken into water (5 mL) and purified bypreparative reverse phase HPLC to give the desired product as the bis-trifluoroacetate salt (50 mg), a colorless solid.

Analysis. $^1$M-NMR (DMSO-d$_6$): 9.82 (s, 2H), 8.42 (tr, 2H), 7.50 (tr, 2H), 7.45 (s, 8H), 7.35 (s, 4H), 7.30 (d, 4H), 7.18 (d, 4H), 5.00 (s, 4H), 4.21 (d, 4H), 3.20 (q, 4H), 2.30 (tr, 4H). Electrospray LRMS: Calculated for C$_{32}$H$_{40}$N$_{10}$O$_6$: MH$^+$: 660.7; MH$_2^{+2}$/2: 331.4 Found: MH$^+$: 661.5; MH$_2^{+2}$/2: 331.3

EXAMPLE 4

Bis(L-proline-N$^\alpha$-carbonyl)-1,4-dimethanolbenzene

L-proline (1.8 g, 15.6 mmol) was dissolved in water (20 mL) followed by addition of sodium hydroxide (638 mg, 15.6 mmol) and sodium hydrogen carbonate (1.0 g, 11.7 mmol). 1,4-Benzenedimethanol Bischloroformate (1.05 g, 3.9 mmol) was subsequently added to the aqueous solution and the mixture was allowed to stir at room temperature over twelve hours. An additional volume of water (50 mL) was added to the reaction mixture and the diluted solution filtered to remove traces of insoluble residue. The aqueous solution was then acidified to a pH of 1 by dropwise addition of concentrated aqueous hydrochloric acid and the precipitated bis(L-proline-N$^\alpha$-carbonyl)-1,4-dimethanolbenzene collected by filtration. Subsequent washing with water (3×25 mL) and drying in vacuo provided pure bis(L-proline-N$^\alpha$-carbonyl)-1,4-dimethanolbenzene as a colorless foam (1.29 g).

Analysis. $^1$H-NMR (DMSO-d$_6$): 7.40–7.25 (4s, 4H), 5.10–5.00 (m, 4H), 4.20 (2dd, 2H), 3.45–3.30 (m, 4H), 2.30–2.10 (m, 2H), 1.95–1.75 (m, 6H).

Bis((4-aminobenzyl)-L-prolineamide-N$^\alpha$-carbonyl)-1,4-dimethanolbenzene

Bis(L-proline-N$^\alpha$-carbonyl)-1,4-dimethanolbenzene (498 mg, 1.18 mmol), hydroxybenztriazole hydrate (350 mg, 2.60 mmol), and 4-aminobenzylamine (560 μL, 5.0mmol) were dissolved in DMF (5.0 mL) and the resulting yellow solution cooled to 0° C. 1-(3-Dimethylaminopropyl)-3-ethylcarbodiimide hydrochloride (498 mg, 2.60 mmol) was then added to the mixture and allowed to slowly warm to room temperature over twelve hours. Removal of DMF in vacuo followed by addition of water (25 mL) and filtration of the insoluble residue gave bis((4-aminobenzyl)-L-prolineamide-N$^\alpha$-carbonyl)-1,4-dimethanolbenzene (155 mg) as a white solid which was employed without further purification.

Analysis. $^1$H-MMR (DMSO-d$_6$): 8.30–8.20 (m, 2H), 7.40–7.20 (m, 4H), 6.90–6.80 (dd, 4H), 6.50–6.40 (dd, 4H), 5.10–4.90 (m, 8H), 4.20–4.10 (m, 2H), 4.10–4.00 (m, 4H), 3.50–3.30 (m, 4H), 2.10–2.00 (m, 2H), 1.90–1.70 (m, 6H).

Bis((4-quanidylbenzyl)-L-prolineamide-N$^\alpha$-carbonyl)-1,4-dimethanolbenzene Bis((4-aminobenzyl)-L-prolineamide-N$^\alpha$-carbonyl)-1,4-dimethanolbenzene (275 mg, 0.44 mmol) and cyanamide (1.04 g, 24.7 mmol) were heated neat at 60° C. to give a colorless solution followed by addition of hydrogen chloride (4M in dioxane, 430 μL, 1.76 mmol). The resulting yellow liquid was stirred at 60° C. an additional 1.5 hours followed by cooling to room temperature. Addition of ethyl ether (25 mL) gave an insoluble yellow oil which was repeatedly washed with additional ethyl ether (3×25 mL) to remove residual cyanamide followed by drying in vacuo. The yellow oil was then taken into water (5 mL) and purified by preparative reverse phase HPLC to give the bis-trifluoroacetate salt of the desired product as a colorless solid.

Analysis. $^1$H-NMR (DMSO-d$_6$): 9.80 (s, 2H), 8.60–8.50 (m, 2H), 7.42 (s, 8H), 7.40–7.05 (m, 12H), 5.10–4.95 (m, 4H), 4.30–4.20 (m, 6H), 3.50–3.30 (m, 4H), 2.20–2.10 (m, 2H), 1.90–1.75 (m, 6H). Electrospray LRMS: Calculated for C$_{36}$H$_{44}$N$_{10}$O$_6$: MH$^+$: 713.8; MH$_2^{+2}$/2: 357.4. Found: MH$^+$: 713.9; MH$_2^{+2}$/2: 357.5.

EXAMPLE 5

Bis(L-alanine-N$^\alpha$-carbonyl)-1,4-dimethanolbenzene

L-alanine (1.47 g, 16.5 mmol) was dissolved in water (20 mL) followed by addition of sodium hydroxide (662 mg, 16.5 mmol) and sodium hydrogen carbonate (1.0 g, 11.7 mmol). Bischloroformate (1.12 g, 4.25 mmol) was subsequently added to the aqueous solution and the mixture was allowed to stir at room temperature over twelve hours. An additional volume of water (50 mL) was added to the reaction mixture and the diluted solution filtered to remove traces of insoluble residue. The aqueous solution was then acidified to a pH of 1 by dropwise addition of concentrated aqueous hydrochloric acid and the precipitated diacid bis (L-alanine-N$^\alpha$-carbonyl)-1,4-dimethanolbenzene collected by filtration. Subsequent washing with water (3×25 mL) and drying in vacuo provided pure bis(L-alanine-N$^\alpha$-carbonyl)-1,4-dimethanolbenzene as a colorless solid.

Analysis. $^1$H-NMR (DMSO-d$_6$): 7.60 (d, 2H), 7.35 (s, 4H), 5.01 (s, 4H), 4.00 (m, 2H), 1.25 (d, 6H)

Bis((4-aminobenzyl)-L-alanineamide-N$^\alpha$-carbonyl)-1,4-dimethanolbenzene

Bis(L-alanine-N$^\alpha$-carbonyl)-1,4-dimethanolbenzene (392 mg, 1.06 mmol), hydroxybenztriazole hydrate (300 mg, 2.23 mmol), and 4-aminobenzylamine (500 μL, 4.24 mmol) were dissolved in DMF (5.0 mL) and the resulting yellow solution cooled to 0° C. 1-(3-Dimethylaminopropyl)-3-ethylcarbodiimide hydrochloride (427 mg, 2.23 mmol) was then added to the mixture and allowed to slowly warm to room temperature over twelve hours. Removal of DMF in vacuo followed by addition of water (25 mL) and filtration of the insoluble residue gave bis((4-aminobenzyl)-L-alanineamide-N$^\alpha$-carbonyl)-1,4-dimethanolbenzene as a white solid which was employed without further purification.

Analysis. $^1$H-NMR (DMSO-d$_6$): 8.10 (tr, 2H), 7.35 (d, 2H), 7.30 (s, 4H), 6.85 (d, 4H), 6.45 (d, 4H), 5.00 (s, 4H), 4.05 (d, 4H), 4.00 (m, 2H), 1.20 (d, 6H).

Bis((4-guanidylbenzyl)-L-alanineamide-N$^\alpha$-carbonyl)-1,4-dimethanolbenzene Bis((4-aminobenzyl)-L-alanineamide-N$^\alpha$-carbonyl)-1,4-dimethanolbenzene (121 mg, 0.22 mmol) and cyanamide (580 mg, 13.8 mmol) were heated neat at 60° C. to give a colorless solution followed by addition of hydrogen chloride (4M in dioxane, 220 μL, 0.88 mmol). The resulting yellow liquid was stirred at 60° C. an additional 2.0 hours followed by cooling to room temperature. Addition of ethyl ether (25 mL) gave an insoluble yellow oil which was repeatedly washed with additional ethyl ether (3×25 mL) to remove residual cyanamide followed by drying in vacuo. The yellow oil was then taken into water (5 mL) and purified by preparative reverse phase HPLC to give the desired product as a bis-trifluoroacetate salt, a colorless solid.

Analysis. $^1$H-NMR (DMSO-d$_6$): 9.75 (s, 2H), 8.40 (tr, 2H), 7.41 (d, 2H), 7.40 (s, 8H), 7.30 (s, 4H), 7.25 (d, 4H), 7.15 (d, 4H), 5.00 (dd AB, 4H), 4.25 (d, 4H), 4.05 (m, 2H), 1.20 (d, 6H). Electrospray LRMS: Calculated for C$_{32}$H$_{40}$N$_{10}$O$_6$: MH$^+$: 661.7; MH$_2^{+2}$/2: 331.4. Found: MH$^+$: 661.6; MH$_2^{+2}$/2: 331.5

EXAMPLE 6

Bis(D-alanine-N$^\alpha$-carbonyl)-1,4-dimethanolbenzene

D-alanine (1.58 g, 17.8 mmol) was dissolved in water (20 mL) followed by addition of sodium hydroxide (711 mg, 17.8 mmol) and sodium hydrogen carbonate (1.1 g, 13.4 mmol). Bischloroformate (1.15 g, 4.36 mmol) was subsequently added to the aqueous solution and the mixture was allowed to stir at room temperature over twelve hours. An additional volume of water (50 mL) was added to the reaction mixture and the diluted solution filtered to remove traces of insoluble residue. The aqueous solution was then acidified to a pH of 1 by dropwise addition of concentrated aqueous hydrochloric acid and the precipitated diacid bis (D-alanine-N$^\alpha$-carbonyl)-1,4-dimethanolbenzene collected by filtration. Subsequent washing with water (3×25 mL) and drying in vacuo provided pure bis(D-alanine-N$^\alpha$-carbonyl)-1,4-dimethanolbenzene as a colorless solid.

Analysis. $^1$H-NMR (DMSO-d$_6$): 7.60 (d, 2H), 7.35 (s, 4H), 5.01 (s, 4H), 4.00 (m, 2H), 1.25 (d, 6H)

Bis((4-aminobenzyl)-D-alanineamide-N$^\alpha$-carbonyl)-1,4-dimethanolbenzene D-alanine derived diacid bis(D-alanine-N$^\alpha$-carbonyl)-1,4-dimethanolbenzene (390 mg, 1.05 mmol), hydroxybenztriazole hydrate (300 mg, 2.23 mmol), and 4-aminobenzylamine (500 µL, 4.24mmol) were dissolved in DMF (5.0mL) and the resulting yellow solution cooled to 0° C. 1-(3-Dimethylaminopropyl)-3-ethylcarbodiimide hydrochloride.(427 mg, 2.23 mmol) was then added to the mixture and allowed to slowly warm to room temperature over twelve hours. Removal of DMF in vacuo followed by addition of water (25 mL) and filtration of the insoluble residue gave bis((4-aminobenzyl)-D-alanineamide-N$^\alpha$-carbonyl)-1,4-dimethanolbenzene as a white solid which was employed without further purification.

Analysis. $^1$H-NMR (DMSO-d$_6$): 8.10 (tr, 2H), 7.35 (d, 2H), 7.30 (s, 4H), 6.85 (d, 4H), 6.45 (d, 4H), 5.00 (s, 4H), 4.05 (d, 4H), 4.00 (m, 2H), 1.20 (d, 6H).

Bis((4-aminobenzyl)-D-alanineamide-N$^\alpha$-carbonyl)-1,4-dimethanolbenzene Bis((4-aminobenzyl)-D-alanineamide-N$^\alpha$-carbonyl)-1,4-dimethanolbenzene (121 mg, 0.22 mmol) and cyanamide (570 mg, 13.6mmol) were heated neat at 60° C. to give a colorless solution followed by addition of hydrogen chloride (4M in dioxane, 220 µL, 0.88 mmol). The resulting yellow liquid was stirred at 60° C. an additional 1.5 hours followed by cooling to room temperature. Addition of ethyl ether (25 mL) gave an insoluble yellow oil which was repeatedly washed with additional ethyl ether (3×25 mL) to remove residual cyanamide followed by drying in vacuo. The yellow oil was then taken into water (5 mL) and purified by preparative reverse phase HPLC to give the desired product as the bis-trifluoroacetate salt, a colorless solid.

Analysis. $^1$H-NMR (DMSO-d$_6$): 9.75 (s, 2H), 8.40 (tr, 2H), 7.41 (d, 2H), 7.40 (s, 8H), 7.30 (s, 4H), 7.25 (d, 4H), 7.15 (d, 4H), 5.00 (dd AB, 4H), 4.25 (d, 4H), 4.05 (m, 2H), 1.20 (d, 6H). Electrospray LRMS: Calculated for C$_{32}$H$_{40}$N$_{10}$O$_6$: MH$^+$: 661.7; MH$_2^{+2}$/2: 331.4 Found: MH$^+$: 661.6; MH$_2^{+2}$/2: 331.5

EXAMPLE 7

Bis(L-phenylalanine-N$^\alpha$-carbonyl)-1,4-dimethanolbenzene

L-Phenylalanine (2.52 g, 15.3 mmol) was dissolved in water (20 mL) followed by addition of sodium hydroxide (610 mg, 15.3 mmol) and sodium hydrogen carbonate (1.28 g, 11.5 mmol). Bischloroformate (1.0 g, 3.8 mmol) was subsequently added to the aqueous solution and the mixture was allowed to stir at room temperature over twelve hours. An additional volume of water (50 mL) was added to the reaction mixture and the diluted solution filtered to remove traces of insoluble residue. The aqueous solution was then acidified to pH=1 by dropwise addition of concentrated aqueous hydrochloric acid and the precipitated diacid bis (L-phenylalanine-N$^\alpha$-carbonyl)-1,4-dimethanolbenzene collected by filtration. Subsequent washing with water (3×25 mL) and drying in vacuo provided pure bis(L-phenylalanine-N$^\alpha$-carbonyl)-1,4-dimethanolbenzene as a colorless solid.

Analysis. $^1$H-NMR (DMSO-d$_6$): 7.68 (d, 2H), 7.30–7.15 (m, 14H), 4.95 (dd AB, 4H), 4.22–4.12 (m, 2H), 3.05 (dd, 2H), 2.80 (dd, 2H).

Bis((4-aminobenzyl)-L-phenylalanineamide-N$^\alpha$-carbonyl)-1,4-dimethanolbenzene L-phenylalanine derived bis(L-phenylalanine-N$^\alpha$-carbonyl)-1,4-dimethanolbenzene (507 mg, 0.97 mmol), hydroxybenztriazole hydrate (299 mg, 2.21 mmol), and 4-aminobenzylamine (460 µL, 4.1 mmol) were dissolved in DMF (5.0 mL) and the resulting yellow solution cooled to 0° C. 1-(3-Dimethylaminopropyl)-3-ethylcarbodiimide hydrochloride (415 mg, 2.17 mmol) was then added to the mixture and allowed to slowly warm to room temperature over twelve hours. Removal of DMF in vacuo followed by addition of water (25 mL) and filtration of the insoluble residue gave bis((4-aminobenzyl)-L-phenylalanineamide-N$^\alpha$-carbonyl)-1,4-dimethanolbenzene as a white solid which was employed without further purification.

Analysis. $^1$H-NMR (DMSO-d$_6$): 8.30 (tr, 2H), 7.50 (d, 2H), 7.30–7.10 (m, 14H), 6.85 (d, 4H), 6.50 (d, 4H), 4.95 (br s, 8H), 4.30–4.20 (m, 2H), 4.10 (d, 4H), 2.95 (dd, 2H), 2.75 (dd, 2H).

Bis(4-quanidylbenzyl)-L-phenylalanineamide-N$^\alpha$-carbonyl)-1,4-dimethanolbenzene Bis((4-aminobenzyl)-L-phenylalanineamide-N$^\alpha$-carbonyl)-1,4-dimethanolbenzene (249 mg, 0.32 mmol) and cyanamide (1.15 g, 27.4 mmol) were heated neat at 60° C. to give a colorless solution followed by addition of hydrogen chloride (4M in dioxane, 320 µL, 1.28 mmol). The resulting yellow liquid was stirred at 60° C. an additional 1.5 hours followed by cooling to room temperature. Addition of ethyl ether (25 mL) gave an insoluble yellow oil which was repeatedly washed with additional ethyl ether (3×25 mL) to remove residual cyanamide followed by drying in vacuo. The yellow oil was then taken into water (5 mL) and purified by preparative reverse phase HPLC to give the desired product as a bis-trifluoroacetate salt, a colorless solid.

Analysis. $^1$H-NMR (DMSO-d$_6$): 9.70 (s, 2H), 8.60 (tr, 2H), 7.58 (d, 2H), 7.40 (s, 8H), 7.30–7.10 (m, 14H), 4.90 (dd AB, 4H), 4.30–4.20 (m, 6H), 2.95 (dd, 2H), 2.75 (dd, 2H). Electrospray LRMS: Calculated for $C_{44}H_{48}N_{10}O_6$: $MH^+$: 813.9; $MH_2^{+2}/2$: 407.5. Found: $MH^+$: 814.0; $MH_2^{+2}/2$: 407.6

EXAMPLE 8

N,N'-bis(N-(4-aminomethylbenzyl)-succinamido)-p-xylylenediamide

A solution of dimethyl succinate (1.46 gm, 10.72 mmol) and p-xylylenediamine (7.9 gm, 54 mmol) was allowed to stir overnight at room temperature (R.T.) then heated to 90° C. for 16 h. The reaction mixture was cooled, diluted with EtOAc and washed with 1N HCl. The organic layer was dried and concentrated to a yellow solid. The solid was washed with hexanes twice and dried in vacuo. The diamide (0.05 gm, 0.137 mmol) and p-xylylene diamine (0.187 gm, 1.37 mmol) were heated at 67° C. for 48 h. The solid residue was mixed with water and stirred vigorously. The suspension was centrifuged, and the water decanted. Another portion of water was added and the residue stirred and centrifuged. The water was decanted, and MeOH was added. The material was stirred and centrifuged, the MeOH decanted. The residue was dried to an off-white solid. This was dissolved in HOAc and precipitated with EtOAc. The desired compound was purified by prep HPLC, 30 mg at a time, 4 injections (2–27% ACN/water). A single peak was collected and lyophilized to a white solid (90 mg).

EXAMPLE 9

N,N'-Bis(N-(4-aminomethylbenzl)-malonamido)-p-xylylene diamide p-Xylylene diamine (1.0 g, 7.4 mmol) was melted at 67° C. Diethyl malonate (0.372 mL, 2.5 mmol) was added with stirring. The mixture was stirred at 67° C. under nitrogen atmosphere overnight (ca. 18 h). Water (30 mL) was added and this mixture was stirred briefly. The mixture was centrifuged at 1500 rpm for 10 min and the water was decanted. Water (25 mL) was added and this mixture was stirred briefly. The mixture was centrifuged for 10 min and the water was decanted. Acetic acid (10 mL) and diethyl ether (40 mL) were added. The mixture was centrifuged for 10 minutes. The liquid was decanted. Diethyl ether (10 mL) was added, the mixture was stirred, and the ether was decanted. The compound was dried under vacuum. From the residue, 30 mg was separated by preparatory liquid chromatography (Prep LC) on a 5–30% ACN/Water 0.1% TFA gradient over 30 min to yield 6 mg of the bis-TFA salt of the title compound.

Analysis. $^1H$ NMR (CDCl$_3$) δ 7.4(s), 7.3(s), 4.45(s), 4.40(s), 4.35(s), 4.1(s), 3.3(s). Calculated mass for $C_{30}H_{36}N_6O_4$: 544.3236, found [M+1]=545.8 and [M+2]/2= 273.5.

EXAMPLE 10

N,N'-Bis(N-aminomethylbenzyl)glutaramido)-p-xylylene diamide p-Xylylene diamine (1.0g, 7.4 mmol) was heated to 67° C. Dimethyl glutarate (0.36 mL, 2.5 mmol) was added with stirring. The mixture was stirred at 67° C. under nitrogen atmosphere overnight (ca. 18 h). Water (30 mL) was added and this mixture was stirred briefly. The mixture was centrifuged at 1500 rpm for 10 min and the water was decanted. Water (30 mL) was added and this mixture was stirred briefly. The mixture was centrifuged for 10 min and the water was decanted. Acetic acid (5 mL) and diethyl ether (40 mL) were added. The mixture was centrifuged for 10 minutes. The liquid was decanted. Diethyl ether (10 mL) was added, the mixture was stirred, and the ether was decanted. The compound was dried under vacuum. From the residue, 30 mg was separated by PrepLC on a 5–30% ACN/Water 0.1% TFA gradient over 30 min to yield 5 mg of the bis-TFA salt of the title compound.

From the peak at 22.1 min, the desired compound was characterized: $^1H$ NMR (CDCl$_3$) 6 7.21(d, J=3 Hz), 7.19(d, J=3 Hz), 4.25(s), 4.21(s), 3.96 (s), 2.17(m), 1.80(m). Calculated mass for $C_{34}H_{44}N_6O_4$: 600.3872, found [M+1]= 601.8 and [M+2]/2=301.5.

EXAMPLE 11

N,N'-Bis(N-(3-aminomethylbenzyl)succinamido)-m-xylylene diamide m-Xylylene diamine (1.0 g, 7.4 mmol) was stirred at room temperature. Dimethyl succinate (0.320 mL, 2.5 mmol) was added with stirring. The mixture was stirred at room temperature over weekend (ca. 66 h). Water (25 mL) was added and this mixture was stirred briefly. The mixture was centrifuged at 1500 rpm for 10 min and the water was decanted. Water (25 mL) was added and this mixture was stirred briefly. The mixture was centrifuged for 10 min and the water was decanted. Acetic acid (5 mL) and diethyl ether (40 mL) were added. The mixture was centrifuged for 10 minutes. The liquid was decanted. Diethyl ether (10 mL) was added, the mixture was stirred, and the ether was decanted. The compound was dried under vacuum. From the residue, 30 mg was separated by PrepLC on a 0–25% ACN/Water 0.1% TFA gradient over 30 min to yield 3 mg of the bis-TFA salt of the title compound.

From the peak at 34.4 min, the desired compound was characterized: $^1H$ NMR (D$_2$O) δ 7.2(m), 4.35(s), 4.25(s), 4.05(s), 2.6(s). Calculated mass for $C_{32}H_{40}N_6O_4$: 572.3554, found [M+1]=573.7 and [M+2]/2=287.5.

EXAMPLE 12

N,N'-Bis(N-(4-aminomethylbenzamido)-4-aminobutyric)-p-xylylene diamide

To a solution of 4-aminobutyric acid (440 mg, 4.3 mmol, 1.0 equiv) and sodium hydroxide (188 mg, 4.7 mmol, 1.1 equiv) in THF (25 mL) and water (25 mL) was added benzyl chloroformate (0.630 mL, 4.4 mmol, 1.0 equiv). After 45 min, more sodium hydroxide (175 mg, 4.4 mol, 1.0 equiv) was added. The solution was stirred for 3 h and concentrated in vacuo. Water was added, and the mixture was washed three times with dichloromethane, three times with ethyl acetate, and concentrated.

To the residue (416 mg) in dichloromethane (20 mL) was added p-xylene diamine (116 mg, 0.85 mmol, 0.48 equiv) and DMF (3 mL). The solution was cooled to 0° C., and hydroxybenzotriazole hydrate (HOBT, 243 mg, 1.8 mmol, 1.0 equiv) and Dimethylaminopropylethyl carbodiimide HCl (EDC, 338 mg, 1.8 mmol, 1.0 equiv) were added. N-Methyl morpholine (NMM, 30 drops) was added, and the solution was stirred at 0° C. for 1 h and overnight at room temperature. Dichloromethane was added and the solution was washed with 0.2N HCl. A precipitate was filtered from the acid layer.

To this precipitate was added ethanol and palladium (5% on carbon, 238 mg). The mixture was stirred under hydrogen (1 atm) overnight. The mixture was filtered and the ethanol layer was concentrated in vacuo to yield crude diamide.

To a solution of di-tert-butyl dicarbonate (1.2 g, 8.0 mmol, 1 equiv) in tetrahydrofuran (15 mL) was added a solution of 4-(aminomethyl)benzoic acid (1.9 g, 8.7 mmol, 1.1 equiv) in tetrahydrofuran (35 mL). The solution was stirred for 24 hours. The solution was concentrated in vacuo. Water (50 mL) was added and decanted. A solution of 0.1N HCl was added (50 mL). The product, N-Boc-4-(aminomethyl) benzoic acid was removed by filtration and dried in vacuo.

To the crude diamide (227 mg) in DMF (10 mL) at 0° C. were added HOBT (228 mg, 1.7 mmol, 2.3 equiv), EDC (324 mg, 1.7 mmol, 2.3 equiv), N-Boc-4-(aminomethyl) benzoic acid (311 mg, 1.3 mmol, 1.8 equiv), and NMM (30 drops). The solution was stirred at 0° C. for 20 min and at 50° C. overnight. The solution was washed with 0.1N HCl, saturated aqueous sodium bicarbonate, and brine. The organic layer was dried over magnesium sulfate, filtered, and concentrated in vacuo.

To 100 mg of the crude compound was added dichloromethane (10 mL) and TFA (10 mL). The solution was stirred for 1 h and concentrated in vacuo. The residue was rinsed twice with ether and dried under vacuum. The crude product was purified on Waters LC (2–30% acetonitrile in water) and further purified on Gilson LC (2–27% acetonitrile in water) to yield 2 mg of >95% pure biS-TFA salt of the title compound.

Analysis. $^1$H NMR ($D_2O$): 7.6 (d, J=9 Hz, 4H), 7.4 (d, J=9 Hz, 4H), 7.1 (s, 4H), 4.2 (s, 4H), 4.15 (s, 4H), 3.3 (t, J=7 Hz, 4H), 2.3 (t, J=7 Hz, 4H), 1.9 (m, 4H). Mass Spectrum: calcd mass for $C_{32}H_{40}N_6O_4$: 572.3554, found: [M+1]=537.5, [M+2]/2=287.3.

EXAMPLE 13

Bis(p-xylylenediamine-L-alanine)-1,4-benzenedimethanol dicarbamate

To a solution of p-xylylene diamine (5.4 g, 40 mmol, 8 equiv) in 1,4-dioxane (50 mL) was added dropwise a solution of Boc anhydride (1.09 g, 5 mmol, 1 equiv) in 1,4-dioxane (30 mL). The solution was stirred for 3 days. The solvent was removed in vacuo. The residue was dissolved in water and filtered. The aqueous layer was extracted with dichloromethane (4×25 mL). The combined organic layers were dried over $MgSO_4$, filtered, and concentrated in vacuo. Dichloromethane (50 mL) was added. The solution was washed with water (3×50 mL), dried over $MgSO_4$, filtered, and concentrated in vacuo to yield mono-Boc xylylene diamine.

To a solution of mono-Boc xylylene diamine (116 mg, 0.49 mmol, 2.2 equiv) in dichloromethane (20 mL) at 0° C. was added previously synthesized L-alanine-benzenedimethanol dicarbamate (80 mg, 0.22 mmol, 1 equiv), EDC (94 mg, 0.49 mmol, 2.2 equiv), and HOBT (72 mg, 0.53 mmol, 2.4 equiv). NMM (30 drops) and DMF (1 mL) were added. The solution was stirred at 0° C. for 1 hour and at r.t. overnight. The solution was washed with 0.1N HCl, saturated aqueous sodium bicarbonate, and brine. The organic layer was concentrated in vacuo. TFA and dichloromethane (10 mL each) were added and the solution was stirred for ½ h. The solution was concentrated under vacuum and rinsed twice with ether. The crude product was purified on the Waters LC (2–30% gradient) to yield >24 mg of ≧96% pure bis HCl salt of the title compound.

Analysis. $^1$H NMR ($D_2O$) δ 7.4–7.2 (m, 12H), 5.1 (s, 4.4H), 4.4–4.0 (m, 10.7H) 1.3 (broad s, 6.3H). Mass Spectrum: calcd mass for $C_{32}H_{40}N_6O_6$ 604.7062, found [M+1]=605.8, [M+2]/2=303.6.

EXAMPLE 14

Bis(p-xylylenediamine-D-alanine)-1,4-benzenedimethanol dicarbamate

This compound was prepared in the same manner as described in Example 13, except using D-alanine-benzenedimethanol.

EXAMPLE 15

N,N'-Bis(N-(4-aminomethylbenzyl)butyramido) terephthalamide

Benzyl chloroformate (0.630 mL, 753 mg, 4.4 mmol, 1 equiv) and 4-aminobutyric acid (440 mg, 4.3 mmol, 1 equiv) were added to a solution of NaOH (188 mg, 4.7 mmol, 1.1 equiv) in THF-water (25 mL each). More NaOH (175 mg, 4.4 mmol, 1 equiv) was added to make pH>7. The solution was stirred for 3 h. The solution was concentrated in vacuo. Water was added and the solution was washed three times each with dichloromethane and ethyl acetate. The aqueous layer was concentrated in vacuo to yield N-Cbz-4-aminobutyric acid. To a solution of mono-Boc p-xylylene diamine (271 mg, 1.1 mmol, 1 equiv) in dichloromethane (25 mL) was added N-Cbz-4-aminobutyric acid (258 mg, 1.1 mmol, 1 equiv). The mixture was cooled to 0° C. HOBT (165 mg, 1.2 mmol, 1.1 equiv) and EDC (233 mg, 1.2 mmol, 1.1 equiv) were added. NMM (30 drops) was added to adjust pH. The solution was stirred at 0° C. for 1 h and at r.t. over the weekend. Dichloromethane was added, and the solution was washed with 0.05N HCl, saturated aqueous sodium bicarbonate, and brine. The organic layer was dried over $MgSO_4$, filtered, and concentrated in vacuo. Ethanol (30 mL) and palladium (270 mg, 5%/C) were added to the residue (432 mg) and the mixture was stirred under hydrogen (1 atm) for 20 h. The mixture was filtered, and the ethanol was removed in vacuo. To the residue (206 mg, 0.64 mmol, 2.1 equiv) was added dichloromethane (25 mL) and DMF (2 mL). Triethylamine (0.091 mL, 66 mg, 0.65 mmol, 2.2 equiv) and terephthaloyl dichloride (60 mg, 0.3 mmol, i equiv) were added and the solution was stirred overnight. The solution was washed with 0.05N HCl, saturated aqueous sodium bicarbonate, and brine. The organic layer was concentrated in vacuo. TFA and dichloromethane (10 mL each) were added and the solution was stirred for 1 h. The solution was concentrated under vacuum and rinsed twice with ether. The crude product was purified on the Waters LC (2–30% gradient) to yield 50 mg of >95% pure bis TFA salt of the title compound.

Analysis. $^1$NMR ($D_2O$) δ 7.7 (s, 4H), 7.3 (d, J=9 Hz, 4H), 7.2 (d, J=9 Hz, 4H), 4.2 (s, 4H), 4.0 (s, 4H), 3.4 (t, J=6 Hz, 4H), 2.4 (t, J=6 Hz, 4H), 1.9 (m, 4H). Mass Spectrum: calcd mass for $C_{32}H_{40}N_6O_4$ 572.7074, found [M+1]=573.7, [M+2]/2=286.2.

EXAMPLE 16

N,N'-Bis(4-aminomethylbenzamidoethylene)-1,4-benzenedimethanol dicarbamate

Ethylene diamine (2.67 mL, 2.4 g, 40 mmol, 8 equiv) was dissolved in basic alumina-filtered dioxane (40 mL). Boc anhydride (1091 mg, 5 mmol, 1 equiv) in dioxane (30 mL) was added dropwise. The solution was stirred for 24 h. The solution was concentrated in vacuo. The residue was dissolved in water and filtered. The aqueous layer was extracted three times with dichloromethane. The combined organic layers were dried over MgSO$_4$, filtered, and concentrated in vacuo to yield an oil. The mono-Boc ethylene diamine (210 mg, 1.3 mmol, 2.2 equiv) was dissolved in dichloromethane (12 mL). Triethylamine (0.199 mL, 144 mg, 1.4 mmol, 2.4 equiv) and previously-synthesized 1,4-benzyl dichloroformate (0.108 mL, 158 mg, 0.6 mmol, 1 equiv) were added. The solution was stirred for 3 days. The solution was washed with 0.015N HCl, saturated aqueous sodium bicarbonate, and brine. The organic layer was concentrated in vacuo. The residue was dissolved in 10 mL each of TFA and dichloromethane and stirred for 1 h. The solution was concentrated in vacuo and the residue was rinsed twice with ether. The product (277 mg, 0.52 mmol, 1 equiv) was dissolved in dichloromethane. P-Boc-aminomethyl benzoic acid (380 mg, 1.5 mmol, 2.9 equiv) was added. HOBT (211 mg, 1.6 mmol, 3 equiv) and EDC (296 mg, 1.5 mmol, 2.9 equiv) were added. DMF (1 mL) and NMM (30 drops) were added. The solution was stirred at 50° C. overnight. The solution was washed with 0.015N HCl, saturated aqueous sodium bicarbonate, and brine. The solution was concentrated in vacuo. The residue was dissolved in 10 mL each of TFA and dichloromethane and stirred for 2 h. The solvent was removed in vacuo and the residue was rinsed twice with ether. The crude product was purified on the Waters LC (2–30% gradient) to yield 5 mg of >95% pure bis TFA salt of the title compound.

Analysis. $^1$H NMR (D$_2$O) δ 7.6 (d, J=7 Hz, 4H), 7.4 (d, J=7 Hz, 4H), 7.1 (s, 4H), 4.95 (s, 4H), 4.2 (s, 4H), 3.4 (m, 4H), 3.3 (m, 4H). Mass Spectrum: calcd mass for C$_{30}$H$_{36}$N$_6$O$_6$ 576.6524, found [M+1]=577.7, [M+2]/2= 289.0.

EXAMPLE 17

N,N'-Bis(N-(4-aminomethylbenzyl)glutaramido)-N, N'-bis(methyl)-p-xylene diamide

Mono-Boc xylene diamine (359 mg, 1.5 mmol, 1 equiv) was dissolved in dichloromethane (15 mL). Triethylamine was added (0.230 mL, 167 mg, 1.65 mmol, 1.1 equiv). Methyl glutaryl chloride (0.208 mL, 248 mg, 1.5 mmol, 1 equiv) was added. The solution was stirred for 3 days. The solution was washed with 25 mL each of 0.015N HCl, saturated aqueous sodium bicarbonate, and brine. The organic layer was dried over MgSO$_4$, filtered, and concentrated in vacuo. The residue (570 mg, 1.5 mmol, 1 equiv) was dissolved in methanol (15 mL). Ba(OH)$_2$ (538 mg, 1.7 mmol, 2.2 equiv) was added. The solution was stirred overnight. A solution of 1N HCl (25 mL) was added to the reaction mixture. The product was extracted three times with dichloromethane. The solvent was removed in vacuo to yield the carboxylic acid (373 mg). The carboxylic acid (179 mg, 0.51 mmol, 1 equiv) was dissolved in dichloromethane (10 mL). N,N'-bis-methyl xylene diamine (111 mg, 0.28 mmol, 0.55 equiv) was added. The solution was cooled to 0° C. DMF (1 mL) was added. EDC (114 mg, 0.59 mmol, 1.2 equiv), HOBT (76 mg, 0.56 mmol, 1.1 equiv), and NMM (30 drops) were added. The solution was stirred at 0° C. for 1 h, and at r.t. for 2 days. The solution was washed with 0.015N HCl, saturated aqueous sodium bicarbonate, and brine. The organic layer was dried over MgSO$_4$, filtered, and concentrated in vacuo. The residue was dissolved in TFA (10 mL) and dichloromethane (10 mL) and stirred for 45 min. The solution was concentrated in vacuo. The crude product was purified on the Waters LC (2–30% gradient) to yield 40 mg of >95% pure bis TFA salt of the title compound.

Analysis. $^1$H NMR (D$_2$O) δ 7.4–7.1 (m, 12H), 4.6–4.0 (m, 12H), 2.9 (s, 6H), 2.4–2.2 (m, 8H), 1.9 (m, 4H). Mass Spectrum: calcd mass for C$_{36}$H$_{48}$N$_6$O$_4$ 628.8149, found [M+1]=629.8.

EXAMPLE 18

Bis(p-xylylenediaminesarcosine)-1,4-benzenedimethanol dicarbamate

Safcosine methyl ester (187 mg, 1.3 mmol, 2.2 equiv) was dissolved in dichloromethane. Triethylamine (0.400 mL, 290 mg, 2.9 mmol, 4.8 equiv) and 1,4-benzyl dichloroformate (0.108 mL, 158 mg, 0.6 mmol) were added. The solution was stirred for 3 days. The solution was washed with 50 mL each of 0.1N HCl, saturated aqueous sodium bicarbonate, and brine. The organic layer was dried over MgSO$_4$, filtered, and concentrated in vacuo. The residue (175 mg, 0.44 mmol) was added to p-xylylene diamine (1.750 g, 12.9 mmol, 14.7 equiv). The mixture was heated to 70° C. overnight. Water was added. The mixture was centrifuged at 2000 rpm for 10 min and the water was decanted. The trituration was repeated with water, acetic acid-ether, and ether. The residue was concentrated in vacuo. The crude product was purified on the Waters LC (2–30% gradient) to yield 66 mg of >95% pure bis TFA salt of the title compound.

Analysis. $^1$H NMR (D$_2$O) δ 7.4–7.1 (m, 12H), 5.0 (s, 3.2H), 4.4–3.9 (m, 11.3H), 2.9 (s, 5.3H). Mass Spectrum: calcd mass for C$_{32}$H$_{40}$N$_6$O$_6$ 604.7062, found [M+1]=605.4, [M+2]/2=303.3.

EXAMPLE 19

N,N'-Bis(4-aminomethylbenzamidopropylene)-1,4-benzenedimethanol dicarbamate

Diaminopropane (3.332 mL, 2.959 g, 40 mmol, 6.9 equiv) was dissolved in basic alumina-filtered dioxane (40 mL). Boc anhydride (1272 mg, 5.8 mmol, 1 equiv) in dioxane (60 mL) was added dropwise. The solution was stirred for 3 days. The solution was concentrated in vacuo. The residue was dissolved in water and filtered. The aqueous layer was extracted three times with dichloromethane. The organic layer was dried over MgSO$_4$, filtered, and concentrated in vacuo to yield an oil. The mono-Boc diaminopropane (248 mg, 1.4 mmol, 2.3 equiv) was dissolved in dichloromethane (12 mL). Triethylamine (0.220 mL, 160 mg, 1.6 mmol, 2.6 equiv) and previously-synthesized 1,4-benzyl dichloroformate (0.112 mL, 164 mg, 0.62 mmol, 1 equiv) were added. The solution was stirred overnight. The solution was washed with 0.1N HCl, saturated aqueous sodium bicarbonate, and brine. The organic layer was dried over MgSO$_4$, filtered, and concentrated in vacuo to yield a white powder. The powder was dissolved in 10 mL each of TFA and dichloromethane and stirred for 45 min. The solution was concentrated in vacuo and the residue was rinsed twice with ether. The product (122 mg, 0.21 mmol, 0.5 equiv) was dissolved in dichloromethane (20 mL). P-Boc-aminomethyl benzoic acid (105 mg, 0.42 mmol, 1 equiv) was added. HOBT (66 mg, 0.49 mmol, 1.2 equiv) and EDC (92 mg, 0.48 mmol, 1.1 equiv) were added. DMF (2 mL) and NMM (30 drops) were added. The solution was stirred at 0° C. for 30 min, 50° C. overnight, and r.t. for 3 days. The solution was washed with 0.1N HCl, saturated aqueous sodium bicarbonate, and brine. The solution was concentrated in vacuo. The residue was dissolved in 10 mL each of TFA and dichloromethane and stirred for 30 min. The solvent was removed in vacuo and the residue was rinsed twice with ether. The crude product was purified on the Waters LC (2–30% gradient) to yield 20 mg of >95% pure bis TFA salt of the title compound.

Analysis. $^1$H NMR (D$_2$O) 6 7.7 (d, J=9 Hz, 4H), 7.5 (d, J=9 Hz, 4H), 7.3 (s, 4H), 4.95 (s, 4H), 4.2 (s, 4H), 3.3 (t, J=7 Hz, 4H), 3.2 (t, J=7 Hz, 4H) 1.8 (quint, J=7 Hz, 4H). Mass Spectrum: calcd mass for C$_{32}$H$_{40}$N$_6$O$_6$ 604.7062, found [M+1]=605.9, [M+2]/2=303.4.

EXAMPLE 20

N,N'-Bis(N-[4-aminomethylbenzyl)butyramido)-N, N'-bis(methyl)terephthalamide

To a solution of mono-Boc protected p-xylylene diamine (248 mg, 1.05 mmol, 1 equiv) in dichloromethane (20 mL) was added N-Cbz-N-methyl-4-aminobutyric acid (287 mg, 1.14 mmol, 1.1 equiv, prepared in a manner similar to that of N-Cbz-4-amino butyric acid). The mixture was cooled to 0° C. HOBT (171 mg, 1.27 mmol, 1.2 equiv) and EDC (243 mg, 1.2 mmol, 1.2 equiv) were added. NMM (30 drops) was added to adjust pH to >7. The solution was stirred at 0° C. for 1 h and at r.t. overnight. Dichloromethane was added, and the solution was washed with 0.1N HCl, saturated sodium bicarbonate, and brine. The organic layer was dried over MgSO$_4$, filtered, and concentrated in vacuo. Ethanol (25 mL) and palladium (94 mg, 10%/C) were added to the residue and the mixture was stirred under hydrogen (1 atm) for 2.5 h. The mixture was filtered, and the ethanol was removed in vacuo.

To the residue (315 mg, 0.94 mmol, 2.4 equiv) was added dichloromethane (10 mL). Triethylamine (0.144 mL, 105 mg, 1.03 mmol, 2.6 equiv) and terephthaloyl dichloride (81 mg, 0.4 mmol, 1 equiv) were added and the solution was stirred over three days. The solution was washed with 0.05N HCl, saturated aqueous sodium bicarbonate, and brine. The organic layer was dried over MgSO$_4$, filtered, and concentrated in vacuo. TFA and dichloromethane (10 mL each) were added and the solution was stirred for 1 h. The solution was concentrated over vacuum and rinsed twice with ether. The crude product was purified on the Waters LC (2–30% gradient) to yield 30 mg of 90% pure bis HCl salt of the title compound.

Analysis. $^1$H NMR (D$_2$O) 6 7.4–7.2 (m, 12H), 4.4 (d, J=5 Hz, 2H), 4.2 (d, J=2 Hz, 2H), 4.1 (s, 4H), 3.5 (m, 2H), 3.2 (m, 2H), 3.0 (d, J=5 Hz, 3H), 2.9 (d, J=14 Hz, 3H), 2.4 (m, 2H), 2.1 (m, 2H), 1.9 (m, 2H), 1.8 (m, 2H). Mass Spectrum: calcd mass for C$_{34}$H$_{44}$N$_6$O$_4$ 4 600.7612, found [M+1]= 601.9, [M+2]/2=301.6.

EXAMPLE 21

N,N'-Bis(N-(4-aminomethylbenzamido)-N-methyl-4-aminobutyl)-p-xylylene diamide

Benzyl chloroformate (1.570 mL, 1877 mg, 11mmol, 1.1 equiv) and 4-(N-methyl) aminobutyric acid (1530 mg, 10mmol, 1 equiv) were added to a solution of triethylamine (3.832 mL, 2.78 mg, 27.5 mmol, 2.75 equiv) in THF-water (50 mL each). The solution was stirred overnight. Aqueous HCl, 1.5N, was added until a pH of about 1 was reached. The product was extracted with dichloromethane. The organic layer was concentrated in vacuo, dissolved in dichloromethane, and washed with 1.5N HCl. The organic layer was dried over MgSO$_4$, filtered, and concentrated in vacuo.

To a solution of p-xylylene diamine (185 mg, 1.36 mmol, 1.0 equiv) in dichloromethane (30 mL) was added N-Cbz-N-methyl-4-aminobutyric acid (751 mg, 3.0 mmol, 2.2 equiv). The mixture was cooled to 0° C. HOBT (417 mg, 3.1 mmol, 2.3 equiv) and EDC (576 mg, 3.0 mmol, 2.2 equiv) were added. NMM (30 drops) was added to adjust pH to >7. DMF (1 mL) was added. The solution was stirred at 0° C. for 30 min and at r.t. overnight. Dichloromethane (50 mL) was added, and the solution was washed with 0.1N HCl, saturated aqueous sodium bicarbonate, and brine. The organic layer was dried over MgSO$_4$, filtered, and concentrated in vacuo. Ethanol (25 mL) and palladium (94 mg, 10%/C) were added to the residue and the mixture was stirred under hydrogen (1 atm) for 2.5 h. The mixture was filtered, and the ethanol was removed in vacuo. Hydrogenation was repeated overnight with 700 mg palladium.

To a solution of the residue (257 mg, 0.77 mmol, 1.0 equiv) in dichloromethane (20 mL) was added Boc-p-aminomethyl benzoic acid (445 mg, 1.77 mmol, 2.3 equiv). The mixture was cooled to 0° C. HOBT (239 mg, 1.77 mmol, 2.3 equiv) and EDC (340 mg, 1.77 mmol, 2.3 equiv) were added. NMM (30 drops) was added to adjust pH to >7. DMF (2 mL) was added. The solution was stirred at 0° C. for 0.5 h and at 50° C. overnight. Dichloromethane (50 mL) was added, and the solution was washed with 0.1N HCl, saturated aqueous sodium bicarbonate, and brine. The organic layer was dried over MgSO$_4$, filtered, and concentrated in vacuo. TFA and dichloromethane (10 mL each) were added and the solution was stirred for 1.5 h. The solution was concentrated under vacuum and rinsed twice with ether. The crude product was purified on the Waters LC (2–30% gradient) to yield >95% pure bis-HCl salt of the title compound.

Analysis. $^1$H NMR (D$_2$O) 6 7.5–7.1 (m, 12H), 4.4–4.1 (m, 6.4H), 3.5 (m, 1.4H), 3.2 (m, 2.1H), 3.0 (s, 3.5H), 2.9 (s, 2.8H), 2.4 (m, 2.1H), 2.1 (m, 2.1H), 1.9 (m, 2.1H), 1.8 (m, 2.1H). Mass Spectrum: calcd mass for C$_{34}$H$_{44}$N$_6$O$_4$ 600.7612, found [M+1]=601.5, [M+2]/2= 301.5.

EXAMPLE 22

N,N'-Bis(trans-4-aminomethylcyclohexyl-1-amido-propylene)-1,4-benzenedimethanol dicarbamate Diaminopropane (3.332 mL, 2.959 g, 40 mmol, 6.9 equiv) was dissolved in basic alumina-filtered dioxane (40 mL). Boc anhydride (1272 mg, 5.8 mmol, 1 equiv) in dioxane (60 mL) was added dropwise. The solution was stirred for 3 days. The solution was concentrated in vacuo. The residue was dissolved in water and filtered. The aqueous layer was extracted three times with dichloromethane. The combined organic layers were dried over MgSO$_4$, filtered, and concentrated in vacuo to yield an oil.

The mono-Boc diaminopropane (248 mg, 1.4 mmol, 2.3 equiv) was dissolved in dichloromethane (12 mL). Triethylamine (0.220 mL, 160 mg, 1.6 mmol, 2.6 equiv) and previously-synthesized 1,4-benzyl dichloroformate (0.112 mL, 164 mg, 0.62 mmol, 1 equiv) were added. The solution was stirred overnight. The solution was washed with 0.1N HCl, saturated aqueous sodium bicarbonate, and brine. The organic layer was dried over MgSO$_4$, filtered, and concentrated in vacuo to yield a white powder. The powder was dissolved in 10 mL each of TFA and dichloromethane and stirred for 45 min. The solution was concentrated in vacuo and the residue was rinsed twice with ether.

To a solution of trans-4-(aminomethyl)cyclohexane-carboxylic acid (694 mg, 4.4 mmol, 1.0 equiv) in THF (40 mL) was added Boc anhydride (1115 mg, 5.1 mmol, 1.2 equiv). The solution was stirred for three days. Dichloromethane was added and the solution was washed with 0.1N HCl and brine. The organic layer was dried over $MgSO_4$, filtered, and concentrated in vacuo.

To a solution of Boc-trans-4-(aminomethyl)cyclohexane carboxylic acid (545 mg, 2.1 mmol, 1 equiv) in dichloromethane (25 mL) at 0° C. was added diaminopropane benzenedimethanol dicarbamate (106 mg, 0.3 mmol, 15 equiv), EDC (395 mg, 2.05 mmol, 0.98 equiv), and HOBT (270 mg, 2 mmol, 0.95 equiv). NMM (30 drops) and DMF (2 mL) were added. The solution was stirred at 0° C. for 1 hour and at room temperature (r.t.) overnight. The solution was washed with 0.1N HCl, saturated aqueous sodium bicarbonate, and brine. The organic layer was dried over $MgSO_4$, filtered, and concentrated in vacuo. TFA and dichloromethane (10 mL each) were added and the solution was stirred for 1 h. The solution was concentrated under vacuum and rinsed twice with ether. The crude product was purified on the Waters LC (2–30% gradient) to yield 3 mg of 92% pure bis-HCl salt of the title compound.

Analysis. $^1$H NMR ($D_2O$) $\delta$ 7.4 (s, 4H), 5.1 (d, J=18.5 Hz, 3.6H), 3.1 (m, 4.4H), 2.8 (d, J=8 Hz, 4.4H), 2.4–2.2 (m, 1.SH), 2.0 (m, 1.8H), 1.8 (m, 6.2H), 1.6 (m, 4.4H), 1.4 (m, 4.4H), 1.0 (m, 4.4H). Mass Spectrum: calcd mass for $C_{32}H_{52}N_6O_6$ 616.8015, found [M+1]=617.8, [M+2]/2= 309.7.

EXAMPLE 23

N,N'-(Bis(methyl)-bis(N-(4-aminomethyl-benzyl) succinamido)-p-xylylene diamide Sodium hydride (0.22 g, 7.45 mmol, 5.0 equiv) was added to a solution of N,N'-bis(Boc)xylylenediamine (0.50 g, 1.49 mmol, 1.0 equiv) in N,N-dimethylformamide (20 mL) containing 4A sieves at 0° C. Gas evolution was observed. The reaction mixture was stirred at 0° C. for 0.5 h. Iodomethane (0.93 mL, 14.9 mmol, 10 equiv) was added to the reaction mixture, and the resulting grey suspension was stirred at 23° C. for 0.5 h and at 60° C. for 6.5 h. The reaction mixture was carefully quenched with saturated aqueous sodium bicarbonate at 0° C., then partitioned between dichloromethane and water (3×200 mL). The organic layer was dried over sodium sulfate and concentrated to yield crude N,N'-bis(Boc)-bis(methyl)-xylylenediamine as a yellow oil.

Representative Procedure I: A solution of this crude N,N'-bis(Boc)-bis(methyl)xylylenediamine in 50% trifluoroacetic acid in dichloromethane (10 mL) was stirred at 23° C. for 0.5 h. The brown solution was concentrated. Diethyl ether was added to the residue, and the mixture was concentrated. The residue obtained was washed with diethyl ether (two portions), providing the N,N'-bis(methyl)-xylylene diamine bis(trifluoroacetate) as a yellow solid.

Representative Procedure II: 1-(3-Dimethylaminopropyl)-3-ethylcarbodiimide hydrochloride (0.16 g, 0.86 mmol, 3.3 equiv) was added to a mixture of 1-hydroxybenzotriazole hydrate (0.11 g, 0.86 mmol, 3.3 equiv), N,N'-bis(methyl) xylylene diamine bis(trifluoroacetate) (0.10 g, 0.26 mmol, 1.0 equiv), N-(4-N-Boc-aminomethylbenzyl)-amidosuccinic acid (0.26 g, 0.78 mmol, 3.0 equiv), and 4-methylmorpholine (0.20 mL, 1.82 mmol, 7.0 equiv) at 0° C. The pH of the reaction mixture was found to be 8. The yellow suspension was stirred at 0° C. for 1 h and at 23° C. for 20 h. The reaction mixture was partitioned between dichloromethane, 0.05N hydrochloric acid, saturated aqueous sodium bicarbonate, and saturated aqueous sodium chloride. The organic layer was dried over sodium sulfate and concentrated to give crude N,N'-(bis(methyl)-bis(N-(4-N-Boc-aminomethylbenzyl) succinamido)-p-xylylene diamide as a brown residue.

As in Representative Procedure I, a solution of the crude N,N'-(bis(methyl)-bis(N-(4-N-Boc-aminomethylbenzyl) succinamido)-p-xylylene diamide in 50% trifluoroacetic acid in dichloromethane (8 mL) was stirred at 23° C. for 0.5 h, and then concentrated. Diethyl ether was added to the residue, and the mixture was concentrated. The solid obtained was washed with diethyl ether and purified by preparative liquid chromatography, providing N,N'-(bis (methyl)-bis(N-(4-aminomethylbenzyl) succinamido) -p-xylylene diamide bis (trifluoroacetate).

Analysis. $^1$H MMR ($CD_3OD$): 7.40 (s, 8 H); 7.243 (s), 7.241 (s), 7.26 (s), (4 H total); 4.68 (d), 4.58 (d), (4 H total); 4.41 (s, 4 H); 4.10 (s, 4 H); 3.01 (d), 2.90 (d), (6 H total); 2.77 (t, 4 H); 2.58 (t, 4 H). Mass Spectrum: calcd for $C_{34}H_{46}N_6O_4$ ($M(H^+)_2$): 602; found: 602

EXAMPLE 24

N,N'-Bis(N-(4-aminomethylcyclohexylmethyl)-glutaramido)-p-xylylene diamide

Representative Procedure III: A mixture of N,N'-bis (glutaryl)-p-xylylenediamide dimethyl ester (0. 108 g, 0.25 mmol, 1.0 equiv) in 1,4-cyclohexane-bis (methylamine) (1 mL) was stirred at 70° C. for 18 h. The reaction mixture was diluted with water and subjected to centrifugation. The liquid was decanted to give a residue. A mixture of this residue in water was centrifuged, and the liquid decanted. The resulting residue was dried under vacuum over Drierite and purified by preparative liquid chromatography, providing N,N'-bis(N-(4-aminomethylcyclohexylmethyl) glutaramido)-p-xylylene diamide bis(trifluoroacetate).

Analysis. $^1$H NMR ($CD_3OD$): 7.23 (s, 4 H), 4.33 (s, 4 H), 3.03 (d, 4 H), 2.78 (d, 4 H), 2.22 (m, 8 H), 1.83 (m, 12 H), 1.51 (m, 4 H), 0.98 (m, 8 H). Mass Spectrum: calcd for $C_{34}H_{58}N_6O_4$ ($M(H^+)_2$): 614; found: 614.

EXAMPLE 25

N,N'-Bis(methyl)-bis(N-(4-aminomethylcyclohexylmethyl)succinamido)-p-xylylene diamide A solution of di-tert-butyl dicarbonate (5.0 g, 0.023 mol, 1.0 equiv) in tetrahydrofuran (100 mL) was added dropwise over 4 h to a mixture of 1,4-cyclohexane-bis(methylamine) (30 mL, 0.18 mol, 8.0 equiv) in tetrahydrofuran (150 mL). The resulting white suspension was stirred at 23° C. for 24 h, then partitioned between dichloromethane, water (three portions), and saturated aqueous sodium chloride. The organic layer was dried over sodium sulfate and concentrated to give crude N-mono(Boc)-1,4-cyclohexane-bis (methylamine) as a yellow solid.

Representative Procedure IV: 3-Carbomethoxypropionyl chloride (0.17 mL, 1.38 mmol, 1.0 equiv) was added to a biphasic mixture of N-mono(Boc)-1,4-cyclohexane-bis (methylamine) (0.5 g, 2.07 mmol, 1.5 equiv) in dichloromethane (5 mL) and saturated aqueous sodium bicarbonate (5 mL). The reaction mixture was stirred at 23° C. for 23 h, then partitioned between dichloromethane, saturated aqueous sodium bicarbonate, 0.05N hydrochloric acid, and saturated aqueous sodium chloride. The organic layer was dried over sodium sulfate and concentrated, providing crude N-(4-N-Boc-aminomethylcyclohexylmethyl) amidomethylsuccinate (463 mg) as a white solid.

Representative Procedure V: A solution of barium hydroxide octahydrate (0.51 g, 1.63 mmol, 1.25 equiv) in methanol (15 mL) was added to N-(4-N-Boc-aminomethylcyclohexylmethyl)amidomethylsuccinate (463 mg, 1.30 mmol, 1.0 equiv). The reaction mixture was stirred at 23° C. for 17 h, then it was acidified with 1N hydrochloric acid. The mixture was partitioned between dichloromethane (three portions) and water. The combined organic layers were dried over sodium sulfate and concentrated, yielding N-(4-N-Boc-aminomethylcyclohexylmethyl)amidosuccinic acid as a white solid.

N,N'-Bis(methyl)-xylylene diamine bis(trifluoroacetate) (0.100 g, 0.26 mmol, 1.0 equiv) and N-(4-N-Boc-aminomethylcyclohexylmethyl)amidosuccinic acid were coupled in the presence of 1-(3-dimethylaminopropyl)-3-ethyl-carbodiimide hydrochloride and 1-hydroxybenzotriazole hydrate, as in Representative Procedure II. The product obtained was subsequently deprotected to give N,N'-bis(methyl)-bis(N-(4-aminomethylcyclohexyl)succinamido)-p-xylylene diamide bis(trifluoroacetate) in the presence of 50% trifluoroacetic acid in dichloromethane, as in Representative Procedure I, followed by purification via preparative liquid chromatography.

Analysis. $^1$H NMR (CD$_3$OD): 7.21 (s), 7.27 (s), 7.23 (s), 7.12 (s), (4 H total); 4.61 (d), 4.55 (d), (4 H total); 3.20 (m, 4 H); 2.97 (d), 2.86 (d), (6 H total); 2.72 (m, 8); 2.52 (m, 4 H); 1.81 (m, 8 H); 1.50 (m, 4 H); 0.98 (m, 8 H). Mass Spectrum: calcd for C$_{34}$H$_{58}$N$_6$O$_4$ (M(H$^+$)$_2$): 614; found: 614.

EXAMPLE 26

N,N'-Bis(N-(4-aminomethylcyclohexylmethyl)-succinamido)-p-xylylene diamide

N,N'-Bis(N-(4-aminomethylcyclohexylmethyl)-succinamido)-p-xylylene diamide bis (trifluoroacetate) was prepared from N,N'-bis(succinyl)-p-xylylenediamide dimethyl ester in a manner analogous to Representative Procedure III.

Analysis. $^1$H NMR (CD$_3$OD): 8.40 (s, 2 H), 7.99 (s, 2 H), 7.22 (m, 4 H), 4.33 (s, 4 H), 3.02 (s, 4 H), 2.76 (s, 4 H), 2.50 (m, 8 H), 1.83 (s, 8 H), 1.45 (m, 4 H), 0.98 (m, 8 H). Mass Spectrum: calcd for C$_{32}$H$_{54}$N$_6$O$_4$ (M(H$^+$)$_2$): 586; found: 586.

EXAMPLE 27

N,N'-Bis(methyl)-bis(N-(4-aminomethylcyclohexylmethyl)-glutaramido)-p-xylylene didmine N,N'-Bis(methyl)-bis(N-(4-aminomethylcyclohexylmethyl)glutaramido)-p-xylylene didmine bis (trifluoroacetate) was prepared from methyl 4-(chloroformyl)butyrate substituted for 3-carbomethoxypropionyl chloride according to an experimental procedure analogous to that of Example 25.

Analysis. $^1$H NMR (CD$_3$OD): 8.01 (br, 2 H), 7.12 (m, 4 H), 4.57 (m, 4 H), 3.00 (m, 4 H), 2.95 (d, 4 H), 2.88 (s, 2 H), 2.75 (d, 4 H), 2.26 (m, 4 H), 1.84 (m, 12 H), 1.50 (m, 4 H), 0.96 (m, 8 H). Mass Spectrum: calcd for C$_{36}$H$_{62}$N$_6$O$_4$ (M(H$^+$)$_2$): 642; found: 642.

EXAMPLE 28

N,N'-Bis(N-(4-aminomethylbenzyl)-dimethyl-2,3-isopropylidenetartaramido)-p-xylylene diamide A mixture of p-xylylenediamine (0.15 g, 1.10 mmol, 1.0 equiv) and (4R,5R)-(–)-dimethyl 2,3-O-isopropylidene-L-tartrate (2.0 mL, 11.0 mmol, 10 equiv) was stirred at 90° C. for 16 h. The mixture was triturated with 50% hexanes in diethyl ether and diethyl ether (two portions). The residue obtained was partitioned between dichloromethane and water. The organic layer was dried over sodium sulfate and concentrated to give crude N,N'-bis-(dimethyl-2,3-isopropylidene)-p-xylylenediamide dimethyl ester as a brown residue.

A mixture of the crude N,N'-bis(dimethyl-2,3-isopropylidene)-p-xylylenediamide dimethyl ester and p-xylylenediamine (1.5 g) was stirred at 90° C. for 17 h. The reaction mixture was partitioned between dichloromethane and water (three portions). The organic layer was dried over sodium sulfate and concentrated. The resulting residue was purified by preparative liquid chromatography, providing N,N,-bis(N-(4-aminomethylbenzyl)-dimethyl-2,3-isopropylidene-tartaramido)-p-xylylene diamide bis (trifluoroacetate).

Analysis. $^1$H NMR (CD$_3$OD): 7.38 (s, 8 H), 7.25 (s, 4 H), 4.61 (s, 4 s), 4.42 (m, s H), 4.01 (s, 4 s), 1.42 (s, 12 H). Mass Spectrum: calcd for C$_{38}$H$_{50}$N$_6$O$_4$ (M(H$^+$)$_2$): 718; found 718.

EXAMPLE 29

N,N'-Bis(N-(3-aminomethylcyclohexylmethyl)-succinamido)-p-xylylene diamide

N,N'-Bis(N-(3-aminomethylcyclohexylmethyl)-succinamido)-p-xylylene diamide bis(trifluoroacetate) was prepared from 1,3-cyclohexane-bis(methylamine) according to an experimental procedure analogous to that of Representative Procedure III.

Analysis. $^1$H NMR (CD$_3$OD): 8.40 (br, 2 H), 7.97 (br, 2 H), 7.24 (s, 4 H), 4.34 (m, 4 S), 3.02 (m, 4 H), 2.71 (m, 4 H), 2.50 (m, 8 H), 1.78 (m, 6H), 1.50 (m, 6H), 1.26 (m, 2 H), 0.85 (m, 4 H), 0.66 (m, 2H). Mass Spectrum: calcd for C$_{32}$H$_{54}$N$_6$O$_4$ (M(H$^+$)$_2$): 586; found 586.

EXAMPLE 30

N,N,-Bis(N-methyl-N-(4-aminomethylbenzyl)-succinamido)-p-xylylene diamide

Lithium aluminum hydride (1.8 g, 44.5 mmol, 3.5 equiv) was added portionwise to a solution of N-mono(Boc)-p-xylylenediamine in tetrahydrofuran (100 mL) at 0° C. Gas evolution was observed. The grey suspension was stirred at 23° C. for 2 h, by which time gas evolution had ceased. The reaction mixture was refluxed for 16 h, then carefully quenched at 0° C. by the dropwise addition of water (1.8 mL). Gas evolution was seen. 15% Aqueous sodium hydroxide (1.8 mL) and water (5.4 mL) was added dropwise to the suspension at 23° C. The mixture was stirred at 23° C. for 0.5 h, then filtered. The filter cake was washed with tetrahydrofuran and dichloromethane. The filtrate was concentrated, providing crude N-mono(methyl)-p-xylylenediamine (0.68 g) as a yellow oil.

A solution of N-mono(methyl)-p-xylylenediamine (0.10 g, 0.67 mmol, 1.0 equiv) and benzophenone imine (0.11 mL, 0.67 mmol, 1.0 equiv) in dichloromethane (5 mL) was stirred with 4Å sieves at 23° C. for 3 d. The reaction mixture was filtered through celite, and the filtrate was concentrated to give crude N-mono(methyl)-p-xylylenediamine benzophenone imine (190 mg) as a yellow oil.

4-Methylmorpholine (2.0 mL, 18.4 mmol, 2.5 equiv) was added to a mixture of p-xylylenediamine (1.0 g, 7.34 mmol, 1.0 equiv) and succinic anhydride (1.32 g, 13.2 mmol, 1.8 equiv) in N,N-dimethylformamide (25 mL). The reaction mixture was stirred at 50° C. for 22 h. After the mixture was acidified with 1N hydrochloric acid, it was extracted with dichloromethane (three portions). The aqueous layer was filtered. The solid obtained was washed with water and diethyl ether, yielding crude N,N'-bis(succinyl)-p-xylylenediamide diacid (1.83 g) as an off-white solid.

N-Mono(methyl)-p-xylylenediamine benzophenone imine and N,N'-bis(succinyl)-p-xylylenediamide diacid were coupled in the presence of 1-(3-dimethylaminopropyl)-3-ethyl-carbodiimide hydrochloride and 1-hydroxybenzotriazole hydrate as in Representative Procedure II to give N,N'-bis(N-methyl-N-(4-aminomethylbenzyl)succinamido)-p-xylylenediamide di(benzophenone imine).

Representative Procedure VI: Hydroxylamine hydrochloride (20 mg, 0.27 mmol, 5.0 equiv) was added to a solution of N,N'-bis(N-methyl-N-(4-aminomethylbenzyl)-succinamido)-p-xylylene diamide di(benzophenone imine) (49 mg, 0.053 mmol, 1.0 equiv) in tetrahydrofuan (1.0 mL). The yellow solution was stirred at 23° C. for 2.5 h, then concentrated. The residue obtained was washed with diethyl ether (three portions), then purified by preparative liquid chromatography. N,N'-Bis(N-methyl-N-(4-aminomethylbenzyl)succinamido)-p-xylylene diamide bis (trifluoroacetate) was obtained.

Analysis. $^1$H NMR (D$_2$O): 7.28 (m, 12 H), 4.50 (m, 4 H), 4.30 (m, 4 H), 4.10 (s, 4 H), 2.95 (s, 4 H), 2.85 (m, 2 H), 2.60 (m, 8 H). MS: C$_{43}$H$_{46}$N$_6$O$_4$ (M(H$^+$)$_2$): 602; found 602.

EXAMPLE 31

Bis(1,4-cyclohexyldimethylamineglycine)-1,4-benzenedimethanol dicarbamate 1,4-Benzenedimethanol dichloroformate and glycine methyl ester were coupled in the presence of dichloromethane and saturated aqueous sodium bicarbonate as in Representative Procedure IV, providing glycine-1,4-benzenedimethanol dicarbamate dimethyl ester. Following Representative Procedure V, glycine-1,4-benzenedimethanol dicarbamate dimethyl ester was hydrolyzed with barium hydroxide octahydrate to glycine-1,4-benzenedimethanol dicarbamate diacid. N-Mono(Boc)-1,4-cyclohexane-bis(methylamine) and glycine-1,4-benzenedimethanol diacid were coupled in the presence of 1-(3-dimethylaminopropyl)-3-ethylcarbodiimide hydrochloride and 1-hydroxybenzotriazole hydrate, as in Representative Procedure II. The product was deprotected in 50% trifluoroacetic acid in dichloromethane according to Representative Procedure I. Following preparative liquid chromatography, bis(1,4-cyclohexyldimethylamineglycine)-1,4-benzenedimethanol dicarbamate bis(trifluoroacetate) was obtained.

Analsys. $^1$H NMR (CD$_3$OD): 8.00 (br, 2 H), 7.34 (s, 4 H), 5.08 (s, 4 H), 3.72 (s, 4 H), 3.02 (t, 4 H), 2.76 (d, 4 H), 1.80 (d, 8 H), 1.50 (m, 4 H), 1.00 (m, 8 H). Mass Spectrum: calcd for C$_{30}$H$_{50}$N$_6$O$_6$ (M(H$^+$)$_2$): 590; found: 590.

EXAMPLE 32

Bis(1,4-cyclohexyldimethylamine-N-methyl-N-glycine)-1,4-benzenedimethanol dicarbamate Glycine-1,4-benzenedimethanol dicarbamate diacid and N-mono(methyl)-p-xylylenediamine benzophenone imine were coupled as in Representative Procedure II in the presence of 1-(3-dimethylaminopropyl)-3-ethylcarbodiimide hydrochloride and 1-hydroxybenzotriazole hydrate to give bis(1,4-cyclohexyldimethylamine-N-methyl -N-glycine)-1,4-benzene-dimethanol dicarbamate di(benzophenone imine). As in Representative Procedure VI, the di-imine was hydrolyzed in the presence of hydroxylamine hydrochloride. Bis (1,4-cyclohexyl-dimethylamine-N-methyl-N-glycine)-1,4-benzenedimethanol dicarbamate bis(hydrochloride) was obtained after preparative liquid chromatography.

Analysis. $^1$H NMR (CD$_3$OD): 7.35 (m, 12 H), 5.10 (m, 4 H), 4.60 (s, 4 H), 4.05 (d, 8 H), 2.92 (d, 6 H). Mass Spectrum: calcd for C$_{32}$H$_{41}$N$_6$O$_6$ (MH$^+$): 605; found: 605.

EXAMPLE 33

N,N'-Bis(trans-4-aminomethyl-cyclohexyl-1-amidobutyl)-1,4-benzene dimethanol dicarbamate Diaminobutane (2.11 g, 24 mmol, 7.3 equiv) was dissolved in basic alumina-filtered dioxane (75 mL). A solution of Boc anhydride (720 mg, 3.3 mmol, 1 equiv) in dioxane (75 mL) was added dropwise. The reaction mixture was stirred overnight and then concentrated in vacuo. Water was added to the residue. The suspension obtained was filtered. The filtrate was extracted three times with dichloromethane. The combined organic layers were dried over MgSO$_4$, filtered, and concentrated in vacuo to yield an oil.

The N-mono(Boc) diaminobutane (551 mg, 2.9 mmol, 2.2 equiv) was dissolved in dichloromethane (20 mL). Triethylamine (0.420 mL, 3.0 mmol, 2.3 equiv) and previously synthesized 1,4-benzyl dichloroformate (334 mg, 1.3 mmol, 1 equiv) were added. The solution was stirred for 6 h. Dichloromethane (50 mL) was added, and then 0.1N HCl. The product was removed by filtration. The product was dissolved in 10 mL each of TFA and dichloromethane. The solution was stirred for 30 min and concentrated in vacuo.

To a solution of trans-4-(aminomethyl)cyclohexanecarboxylic acid (5.03 g, 32 mmol, 1.0 equiv) in dioxane-water (160 mL each) was added K$_2$CO$_3$ (9.75 g) and Boc anhydride (7.65 g, 35 mmol, 1.1 equiv). The solution was stirred for 6 h. The solution was acidified to pH 3 with 1.5N HCl. The solution was extracted with ethyl acetate (3×100 mL). The combined organic layers were dried over MgSO$_4$, filtered, and concentrated in vacuo.

To a solution of Boc-trans-4-(aminomethyl)cyclohexanecarboxylic acid (418 mg, 1.6 mmol, 1 equiv) in dichloromethane (40 mL) at 0° C. was added diaminobutane benzene dimethanol dicarbamate (<0.73 mmol), EDC (311 mg, 1.6 mmol, >2 equiv), and HOBT (218 mg, 1.6 mmol, >2 equiv). NMM (5 mL) and DMF (2 mL) were added. The solution was stirred at 0° C. for ~1 hour and at r.t. overnight. The solution was washed with 0.1N HCl, saturated aqueous sodium bicarbonate, and brine. The organic layer was concentrated in vacuo. TFA and dichloromethane (10 mL each) were added and the solution was stirred for ~1 h. The solution was concentrated under vacuum and the resulting residue rinsed twice with ether. The crude product was purified on the Waters LC (2–30% gradient) to yield ~30 mg of 98% pure bis(HCl) salt of the title compound.

Analysis. $^1$H NMR (D$_2$O) δ 7.4 (s, 4H), 5.0 (s, 4H), 3.1 (m, 8H), 2.8 (d, J=7 Hz, 4H), 2.1 (m, 2H), 1.8 (d, J=9 Hz, 8H), 1.6 (m, 2H), 1.4 (br, 12H), 1.0 (m, 4H). Mass Spectrum: calcd mass for C$_{24}$H$_{56}$N$_6$O$_6$ 644.8552, found [M+1]=645.7, [M+2]/2=323.4.

EXAMPLE 34

N,N'-Bis[4-(aminomethylbenzamido)butyl]-terephthalyldiamide

A solution of di-tert-butyl dicarbonate (1.2 g, 5.8 mmol) in THF (15 mL) was added dropwise to a solution of diaminobutane (2.9 g, 33 mmol) in THF (35 mL). The mixture was stirred overnight and concentrated in vacuo. Water was added. The suspension was filtered. The filtrate was washed with dichloromethane (3×25 mL). The combined organic layers were washed with water. The organic layer was dried over MgSO$_4$, filtered, and concentrated in vacuo to yield an oil.

The mono(Boc)-diaminobutane (463 mg, 2.5 mmol) was added to a mixture of terephthalic acid (187 mg, 1.1 mmol), EDC (478 mg, 2.5 mmol), HOBT (345 mg, 2.6 mmol), and NMM (50 drops) in DMF (20 mL). The solution was stirred overnight. The reaction mixture was partitioned between EtOAc, 0.1N HCl, 0.2N NaOH, and brine. The organic layer was concentrated in vacuo. The residue was dissolved in 10 mL each of dichloromethane and TFA. The reaction mixture was stirred for 3 h. The solution was concentrated in vacuo. The residue was rinsed twice with ether. Aqueous NaOH (1N) was added, and the solution was extracted with dichloromethane. The aqueous layer was concentrated in vacuo to yield aminobutylterephthalyldiamide.

A solution of di-tert-butyl dicarbonate (2.9 g, 13 mmol) in THF (30 mL) was added dropwise to p-aminomethyl benzoic acid (2 g, 13 mmol) in THF (30 mL). The mixture was stirred overnight and concentrated in vacuo. The Boc-protected p-aminomethyl benzoic acid (209 mg, 0.8 mmol) was combined with aminobutylterephthalyldiamide (180 mg, 0.6 mmol), EDC (167 mg, 0.9 mmol), HOBT (115 mg, 0.9 mmol), and NMM (30 drops) in DMF (10 mL). The solution was stirred for 3 days. The reaction mixture was partitioned between EtOAc, 0.1N HCl, water (three portions), and brine. A portion of the crude product was purified by flash chromatography to yield 25 mg. The purified compound was stirred in dichloromethane (8 mL) and TFA (8 mL) for 2h. The solution was concentrated in vacuo. The residue was rinsed twice with ether. The crude residue was dried over vacuum and purified by Prep LC on a 10–35% gradient of ACN in water (0.1% TFA) to yield 2 mg of >90% pure bis(TFA) salt of the title compound.

Analysis. $^1$H NMR (D$_2$O) d 7.85–7.80 (t, J=7 Hz, 7 H), 7.45 (d, J=9 Hz, 5H), 4.2 (s, 4H), 3.4 (s, 8H), 1.6 (s, 8H); calcd mass for C$_{32}$H$_{40}$N$_6$O$_4$ 572.3554, found [M+1]=573.4, [M+2]/2=287.5.

EXAMPLE 35

N-(3-Aminomethylbenzylsuccinamido)-N'-(4-aminomethyl-benzylsuccinamido)-p-xylylene diamide To a solution of m-xylylene diamine (3.11 mL, 23.6 mmol) in dioxane (30 mL) was added dropwise a solution of di-tert-butyl dicarbonate (675 mg, 3.1 mmol) in dioxane (20 mL). The solution was stirred overnight, and the solvent was removed in vacuo. Water was added, and the suspension obtained filtered. The filtrate was extracted with ethyl acetate (3×20 mL). The combined organic layers were dried over MgSO$_4$, filtered, and concentrated in vacuo to yield the mono-Boc protected meta-xylylene diamine. The same procedure was used to make the mono-Boc p-xylylene diamine.

To a solution of p-xylylene diamine (622 mg, 4.6 mmol) in dichloromethane (10 mL) was added succinic anhydride (1.01 g, 10.1 mmol). The mixture was stirred for 2 days. The solvent was removed in vacuo. The white residue (588 mg) was added to a mixture of N-mono(Boc)-m-xylylene diamine (150 mg, 0.64 mmol), HOBT (120 mg, 0.89 mmol), EDC (168 mg, 0.88 mmol), and NMM (50 drops) in DMF (5 mL) and dichloromethane (10 mL). The solution was stirred for 24 h. Dichloromethane (20 mL) was added, and the solution was washed with 0.2N HCl and water. The organic layer was concentrated in vacuo. Mass spectroscopy showed the presence of a compound with the desired mass.

The diacid (168 mg) was added to a mixture of N-mono(Boc)-p-xylylene diamine (80 mg, 0.34 mmol), HOBT (52 mg, 0.39 mmol), EDC (65 mg, 34 mmol), and NMM (30 drops) in DMF (5 mL). The solution was stirred overnight. The reaction mixture was partitioned between ethyl acetate, 0.1N HCl, water (three portions), and brine. The organic layer was concentrated in vacuo. The product was dissolved in dichloromethane (5 mL) and TFA (5 mL). The solution was stirred for 1.5 h, then concentrated in vacuo. The residue was rinsed twice with ether. The crude residue was dried over vacuum and purified by Prep LC on a 2–27% gradient of ACN in water (0.1% TFA) to yield 3 mg of >98% pure bis(TFA) salt of the title compound.

Analysis. $^1$NMR (D$_2$O) d 7.4–7.1 (m, 12H), 4.3–4.2 (m, 8H), 4.1 (s, 2H), 4.0 (s, 2H); calcd mass for C$_{32}$H$_{40}$N$_6$O$_4$ 572.3554, found [M+1]=573.3, [M+2]/2=287.2.

EXAMPLE 36

N,N'-Bis(N-(4-Guanidylbenzylamine)-malonamido)-p-xylylene diamide p-Xylylenediamine (4.1 g, 30.1 mmol) and triethylamine (12 mL, 86.1 mmol) were taken into dichloromethane (20 mL) and the resulting solution cooled to 0° C. Methyl malonyl chloride (6.4 mL, 60.0 mmol) in dichloromethane (10 mL) was added dropwise to the above solution and the mixture allowed to slowly warm to room temperature over one hour. Concentration in vacuo followed by addition of water (50 mL) and filtration afforded the crude diester. The diester is further purified by recrystallization from methanol/ether to give a colorless solid. $^1$H-NMR (CDCl$_3$): 8.60 (br tr, 2H), 7.20 (s, 4H), 4.25 (d, 4H), 3.60 (s, 6H), 3.30 (s, 4H).

The diester (530 mg, 1.63 mmol) and 4-aminobenzylamine (3.2 mL, 28.6 mmol) were heated neat at 45° C. with stirring over twelve hours to give a yellow solid. The crude mixture was taken up into boiling methanol (50 mL) and the resulting suspension allowed to cool to room temperature. Filtration followed by washing the solid with ether and drying in vacuo gives pure bisaniline as a colorless solid. $^1$H-NMR (CDCl$_3$): 8.45 (tr, 2H), 8.25 (tr, 2H), 7.20 (s, 5 4H), 6.90 (d, 4H), 6.50 (d, 4H), 5.00 (s, 4H), 4.25 (d, 4H), 4.10 (d, 4H), 3.10 (s, 4H).

The bisaniline (20.0 mg, 0.04 mmol) and cyanamide (165 mg, 3.9 mmol) were heated neat at 50° C. to form a homogeneous solution. Hydrogen chloride (4M in dioxane, 50 µL, 0.2 mmol) was added and the mixture was allowed to stir at 50° C. for one hour. Cooling to room temperature followed by addition of ether (25 mL) gave an insoluble yellow oil which was repeatedly washed with additional ether to remove traces of cyanamide. The crude oil was then taken into water (5 mL) and the desired product purified by preparative reverse phase HPLC to give the title compound bis-triflouroacetate salt as a colorless solid.

Analysis. $^1$H NMR (DMSO-d$_6$): 9.75 (s, 2H), 8.55 (tr, 2H), 8.50 (tr, 2H), 7.40 (s, 8H), 7.30 (d, 4H), 7.20 (s, 4H), 7.15 (d, 4H), 4.25 (d, 4H), 4.21 (d, 4H), 3.15 (s, 4H). Electrospray LRMS: Calculated for C$_{30}$H$_{36}$N$_{10}$O$_4$: MH$_2^{+2}$/2: 301.3 Found: MH$_2^{+2}$/2: 301.1.

EXAMPLE 37

N,N'-Bis(N-(4-Guanidylbenzylamino)-succinamido-p-xylylene diamide p-Xylylenediamine (4.6 g, 33.8 mmol) and triethylamine (13.5 mL, 96.9 mmol) were taken into dichloromethane (20 mL) and the resulting solution cooled to 0° C. Methyl succinyl chloride (8.3 mL, 67.6 mmol) in dichloromethane (10 mL) was added dropwise to the above solution and the mixture allowed to slowly warm to room temperature over one hour. Concentration in vacuo and addition of water (50 mL) followed by filtration and washing with warm water several times afforded the pure diester as a colorless solid. $^1$H-NMR (CDCl$_3$): 8.35 (tr, 2H), 7.15 (s, 4H), 4.20 (d, 4H), 3.55 (s, 6H), 2.50 (tr, 4H), 2.40 (tr, 4H).

The diester (580 mg, 1.79 mmol) and 4-aminobenzylamine (2.5 mL, 22 mmol) were heated neat at 45° C. with stirring over twelve hours to give a yellow solid. The crude mixture was taken up into boiling methanol (50 mL) and the resulting suspension allowed to cool to room temperature. Filtration followed by washing the solid with ether and drying in vacuo gives pure bisaniline as a colorless solid. $^1$H-NMR (CDCl$_3$): 8.30 (tr, 2H), 8.10 (tr, 2H), 7.15 (s, 4H), 6.90 (d, 4H), 6.50 (d, 4H), 4.95 (s, 4H), 4.25 (d, 4H), 4.05 (d, 4H), 2.40 (s, 8H).

The bisaniline (91.0 mg, 0.17 mmol) and cyanamide (1.07 g, 25.5 mmol) were heated neat at 50° C. to form a slurry. Hydrogen chloride (4M in dioxane, 100 µL, 0.41 mmol) was added and the mixture was allowed to stir at 50° C. for one hour. Cooling to room temperature followed by addition of ether (25 mL) gave an insoluble yellow solid which was repeatedly washed with additional ether to remove traces of cyanamide. The crude material was then taken into water (5 mL) and the desired product purified by preparative reverse phase HPLC to give the title compound bis-triflouroacetate salt as a colorless solid.

Analysis. $^1$H-NMR (DMSO-d$_6$): 9.70 (s, 2H), 8.40 (tr, 2H), 8.35 (tr, 2H), 7.40 (s, 8H), 7.30 (d, 4H), 7.20 (s, 4H), 7.19 (d, 4H), 4.21 (d, 4H), 4.20 (d, 4H), 2.40 (s, 8H). Electrospray LRMS: Calculated for $C_{32}H_{40}N_{10}O_4$: MH$^+$: 629.7; MH$_2^{+2}$/2: 315.4 Found: MH$^+$: 629.6; MH$_2^{+2}$/2: 315.3.

EXAMPLE 38

N,N'-Bis(N-(4-Guanidylbenzylamino)-glutaramido-p-xylylene diamide p-Xylylenediamine (3.9 g, 28.6 mmol) and triethylamine (12.0 mL, 85.8 mmol) were taken into dichloromethane (40 mL) and the resulting solution cooled to 0° C. Methyl glutaryl chloride (7.9 mL, 57.2 mmol) in dichloromethane (10 mL) was added dropwise to the above solution and the mixture allowed to slowly warm to room temperature over one hour. Concentration in vacuo and addition of water (50 mL) followed by filtration and washing with warm water several times afforded the crude diester as a colorless solid which was employed without further purification. $^1$H-NMR (CDCl$_3$): 8.40 (br tr, 2H), 7.20 (s, 4H), 4.25 (d, 4H), 3.60 (s, 6H), 2.30 (tr, 4H), 2.20 (tr, 4H), 1.85–1.75 (m, 4H).

The crude diester (800 mg, 2.04 mmol) and 4-aminobenzylamine (4.0 mL, 35.2 mmol) were heated neat at 80° C. with stirring over twelve hours to give a yellow solid. The crude mixture was taken up into water (50 mL) to give a yellow suspension. Filtration followed by washing the solid with ethanol then ether and drying in vacuo gave the bisaniline as a tan solid. $^1$H-NMR (CDCl$_3$): 8.30 (br tr, 2H), 8.10 (br tr, 2H), 7.20 (s, 4H), 6.95 (d, 4H), 6.55 (d, 4H), 4.95 (br s, 4H), 4.25 (d, 4H), 4.10 (d, 4H), 2.20 2.05 (m, 6H), 1.80–1.70 (m, 4H).

The bisaniline (150.0 mg, 0.26 mmol) and cyanamide (1.3 g, 30.9 mmol) were heated neat at 65° C. to form a slurry. Hydrogen chloride (4M in dioxane, 200 µL, 0.82 mmol) was added and the mixture was allowed to stir at 65° C. for 30 minutes. Cooling to room temperature followed by addition of ether (25 mL) gave an insoluble yellow solid which was repeatedly washed with additional ether to remove traces of cyanamide. The crude material was then taken into water (5 mL) and the desired product purified by preparative reverse phase HPLC to give the title compound bis-triflouroacetate salt as a colorless solid.

Analysis. $^1$H-NMR (DMSO-d$_6$): 9.75 (s, 2H), 8.40 (tr, 2H), 8.30 (tr, 2H), 7.40 (s, 8H), 7.30 (d, 4H), 7.20 (s, 4H), 7.20 (d, 4H), 4.25 (d, 4H), 4.20 (d, 4H), 2.20–2.10 (m, 8H), 1.80–1.70 (m, 4H). Electrospray LRMS: Calculated for $C_{34}H_{44}N_{10}O_4$: MH$^+$: 656.8; MH$_2^{+2}$/2: 329.4 Found: MH$^+$: 657.7; MH$_2^{+2}$/2: 329.3

Other compounds prepared by methods analogous to those above include, but are not limited to, the following Examples:

| Example No. | Compound |
|---|---|
| 39 | N,N'-Bis((N-(4-aminomethylbenzyl)succinamido))-p-phenethylenediamide |
| 40 | Bis((R,S)-2-(4-guanidinobenzylamino)-2,3-dehydro-6-piperidone)-1,4-benzenedimethanol dicarbamate [isomer 1] |
| 41 | Bis((R,S)-2-(2-(4-guanidinobenzylamino)-2,3-dehydro-6-piperidone)-1,4-benzenedimethanol dicarbmate [isomer 2] |
| 42 | Bis((4-aminomethylanilido)glycine)-1,4-benzenedimethanol dicarbamate |
| 43 | Bis((4-guanidomethylanilido)glycine)-1,4-benzenedimethanol dicarbamate |
| 44 | Bis((3-aminomethylbenzylamido)glycine)-1,4-benzenedimethanol dicarbamate |
| 45 | Bis(trans-1,4-cyclohexyldimethylamine-glycine)-1,4-benzenedimethanol dicarbamate |
| 46 | 4-(Guanidinobenzylamido)glycine-1,4-xylylene diurea |
| 47 | Bis(N-(4-aminomethylbenzyl)glycyl urea)-p-xylylene diamide |
| 48 | N,N-Bis((4-guanidobenzyluriedo)acetyl)]-1,4-xylylene diamide |
| 49 | Bis-[4-N-(4-(aminomethyl)cyclohexylamido)-butyroyl)]-1,4-xylene diamide |
| 50 | Bis(N-(4-aminomethylbenzyl)glycyl urea)-1,4-phenethylenediamide |
| 51 | N,N'-Bis(methyl)-bis(glycine-trans-1,4-cyclohexylbis(methylamine)urea)-p-xylylene diamide |
| 52 | N,N'-Bis(methyl)-bis(glycine-p-xylylenediamine urea)-p-xylylene diamide |
| 53 | N,N'-Bis(methyl)-bis(4-aminomethylbenzoyl-trans-1,4-cyclohexylbis)methylamine)urea)xylylene diamide |
| 54 | N,N'-Bis(methyl)-bis(sarcosine-trans-1,4-cyclohexylbis(methylamine)urea)-p-xylylene diamide |

VI. In Vitro Tryptase Inhibition Assay

The compounds to be assayed (approximately 1 mg) were dissolved in 200 µL dimethylsulfoxide (DMSO) and diluted 1:10 into buffer containing 50 millimolar (mM) Tris-HCl (pH 8.2), 100 mM sodium chloride, and 0.05% polyoxyethylenesorbitan monolaurate (Tween-20°, available from Sigma, St. Louis, Mo.). Seven additional threefold dilutions were made from the initial dilution into the same buffer supplemented with 10% DMSO. Aliquots (50 microliters, µL) from each of the eight dilutions in the series were transferred to individual wells in a 96-well U-bottom microtiter plate. 25 µL of a stock solution of tryptase (1.2 µM, tryptase purified from HMC-1 cells, a human mast cell leukemia line provided by Dr. Joseph Butterfield, see Butterfield et al. (1990) *J. Leukocyte Biol.* 47:409–419; also available commercially from ICN Biomedicals, Irvine, Calif.) was added to each well and the samples were mixed and incubated for one hour at room temperature. The tryptase solution was prepared by placing 60 µg/mL of tryptase into solution with 10 mM MES (2-[N-Morpholino] ethane sulfonic acid) containing 2 mM $CaCl_2$, 20% glycerol and 50 µg/mL heparin. The enzyme reaction was initiated with the addition of the synthetic tripeptide substrate, tosyl-Gly-Pro-Lys-p-nitroanilide (available from Sigma, 25 µL; 0.5 mM final concentration). The microtiter plates were immediately transferred to a UV/MAX Kinetic Microplate Reader (Molecular Devices) and hydrolysis of the chromogenic substrate was followed spectrophotometrically at 405 nanometers (nM) for five minutes. The enzyme assays routinely yielded linear progress curves under these conditions. Initial velocity measurements calculated from the progress curves by a kinetic analysis program (BatchKi; Petr Kuzmic, University of Wisconsin, Madison, Wis.) were used to determine apparent inhibition constants for each inhibitor.

Table II lists the inhibition constants ($K_i$, nanomolar (nM)) which were determined for several of the compounds of the present invention. According to the present invention, a compound was termed "active" or effective as a tryptase inhibitor when its $K_i$ was less than 5000 nM.

TABLE II

| Example # | $K_i$ (nM) |
|---|---|
| 1 | 0.56 |
| 2 | 20.00 |
| 3 | 9.00 |
| 4 | 4000.00 |
| 5 | 289.00 |
| 6 | 364.00 |
| 7 | 227.00 |
| 8 | 3.45 |
| 9 | 150.00 |
| 10 | 8.80 |
| 11 | 127.00 |
| 12 | 86.00 |
| 13 | 31.00 |
| 14 | 366.00 |
| 15 | 11.00 |
| 16 | 396.00 |
| 17 | 14.00 |
| 18 | 5.00 |
| 19 | 5.00 |
| 20 | 107.00 |
| 21 | 1000.00 |
| 22 | 918.00 |
| 23 | 5.00 |
| 24 | 55.00 |
| 25 | 118.00 |
| 26 | 123.00 |
| 27 | 138.00 |
| 28 | 643.00 |
| 29 | 1100.00 |
| 30 | 2300.00 |
| 31 | 12.00 |
| 32 | 874.00 |
| 33 | 48.00 |
| 34 | 222.00 |
| 35 | 19.00 |
| 36 | 682.00 |
| 37 | 40.00 |
| 38 | 100.00 |
| 39 | 6.00 |
| 40 | 463.00 |
| 41 | 611.00 |
| 42 | 783.00 |
| 43 | 8100.00 |
| 44 | 55.00 |
| 45 | 10.00 |
| 46 | 10.00 |
| 47 | 62.00 |
| 48 | 700.00 |

TABLE II-continued

| Example # | $K_i$ (nM) |
|---|---|
| 49 | 366.00 |
| 50 | 43.00 |
| 51 | 130.00 |
| 52 | 79.00 |
| 53 | 1200.00 |
| 54 | 608.00 |

VII. In Vivo Testing

The allergic sheep model of asthma was employed for the in vivo evaluation of the compounds of the invention as antiasthmatics. These methods have been published previously (see Abraham et al. (1983) Am. Rev. Respir. Dis. 128:839–844; Allegra et al. (1983) J. Appl. Physiol. 55:726–730; Russi et al. (1985) J. Appl. Physiol. 59:1416–1422; Soler et al. ((1989) J. Appl. Physiol. 67:406–413. Each sheep serves as its own control. Body weights for these animals ranged from 20–50 kilograms.

In these studies, 2 mg of Compound 2 of the invention was dissolved in buffered saline and the total solution delivered as an aerosol 0.5 hours before, 4 hours after, and 24 hours after antigen challenge (total dose=27; n=6). Compound 2 produced a statistically significant reduction in the early response and attenuated the late response to the antigen challenge as measured by Specific Lung Resistance (SRL). This is shown in FIG. 1. The peak early response was taken as the average of the maximum values occurring immediately post-challenge. Peak late responses were calculated by averaging the maximum response values obtained for each animal within the 6–8 hour time period. This approach is conservative and eliminates the possible reduction in the late response due simply to averaging.

Figure 2:
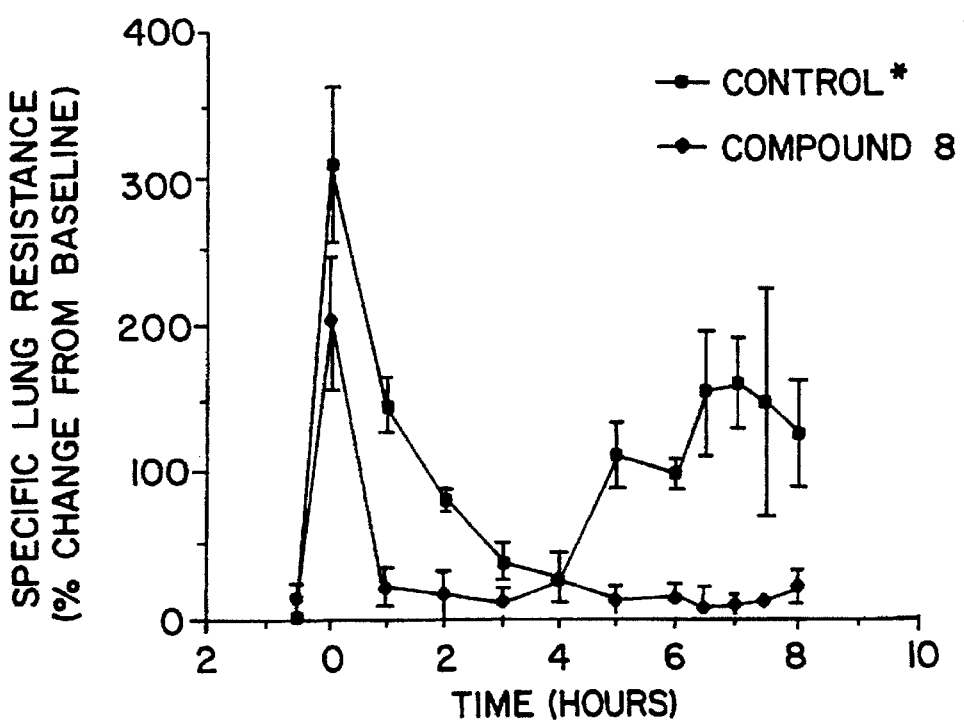
FIG. 2 is a graphical representation of the Specific Lung Resistance (SRL) as a function of time (in hours) of antigen-challenged sheep treated with N,N'-bis((N-(4-aminomethylbenzyl)succinamido))-p-xylylenediamine, Compound 8 of Table II, and sheep treated with a control.

Compound 8 of Table II was administered as just described in a separate experiment. This compound also showed statistically significant early and late increases in SRL (FIG. 2).

Figure 3:
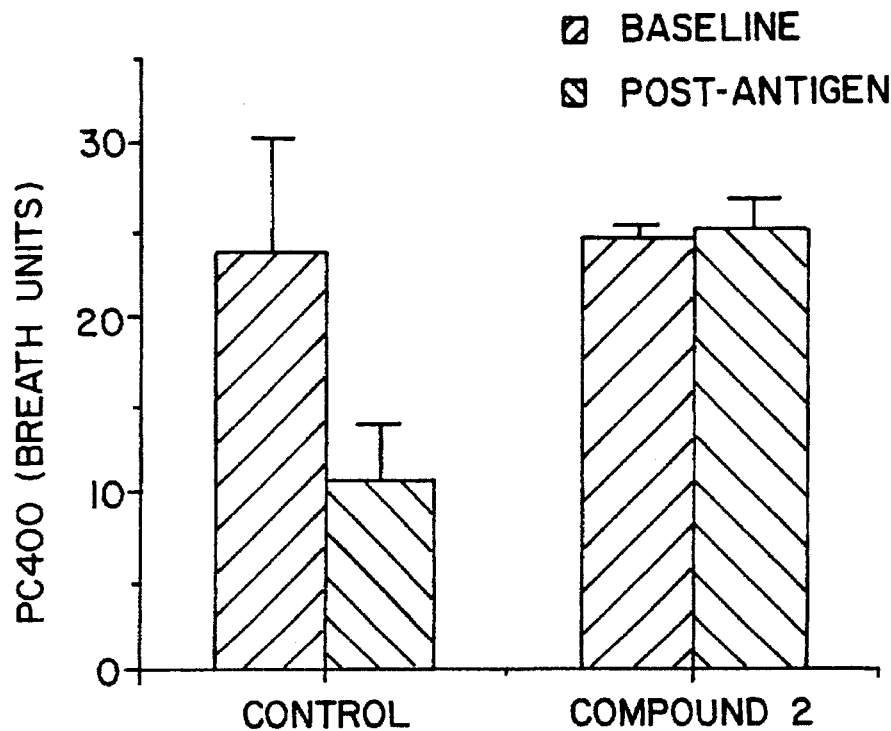
FIG. 3 is a bar chart showing the airway hyperresponsiveness (measured as PC400) antigen-challenged sheep treated with N,N'-bis(4-guanidylbenzylaminecarbonylmethylene)-1,4-benzenedimethanol dicarbamate, Compound 2 of Table II, of the invention versus sheep treated with a control.
Figure 4:
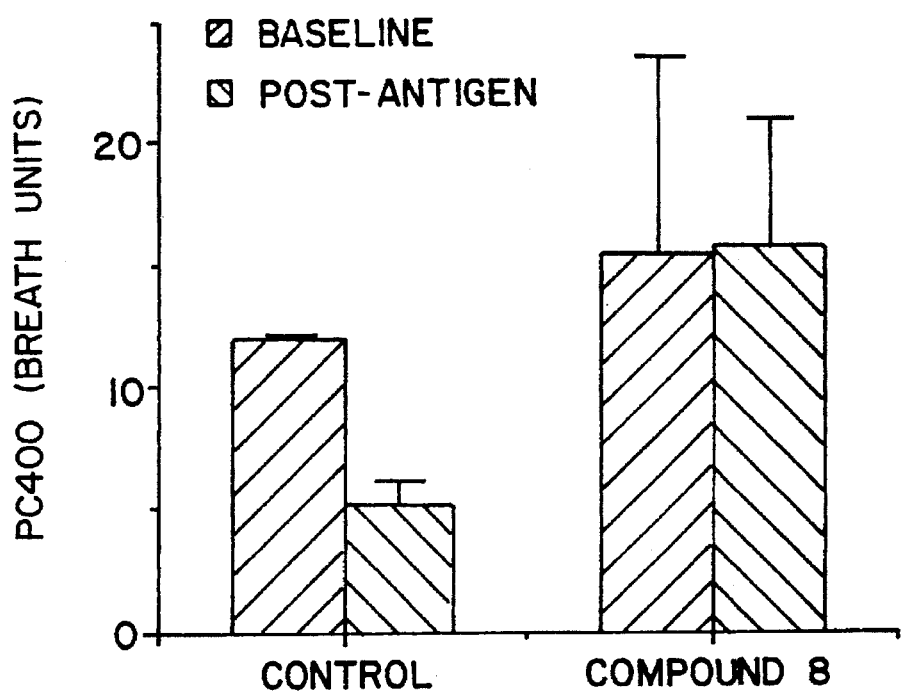
FIG. 4 is a bar chart showing the airway hyperresponsiveness (measured as PC400) antigen-challenged sheep treated with N,N'-bis((N-(4-aminomethylbenzyl)succinamido))-p-xylylenediamine, Compound 8 of Table II, versus sheep treated with a control.

Twenty-four hours after antigen challenge in both the control and drug trial, the sheep developed airway hyperresponsiveness. Airway hyperresponsiveness is expressed as PC400, the concentration of carbachol that causes a 400% increase in SRL; therefore, a decrease in PC400 indicates hyperresponsiveness. Compounds 2 and 8 of Table II both were found to block the onset of hyperresponsiveness. As shown in FIG. 3, Compound 2 maintained the PC400 at the baseline value of 24±6 breath units (p<0.05 vs. baseline). The number of breath units fell to 10±4 for those animals in the control group. As shown in FIG. 4, animals exposed to Compound 8 were found to have greater PC400 values compared to the baseline (15±10 breath units vs. 12±1 breath units in the control). Animals in the control group were found to have only about 5±2 breath units after exposure to antigen challenge. Thus, treatment with either Compound 2 or Compound 8 of the invention resulted in a statistically significant improvement in airway function in antigen challenged sheep.

Figure 5:
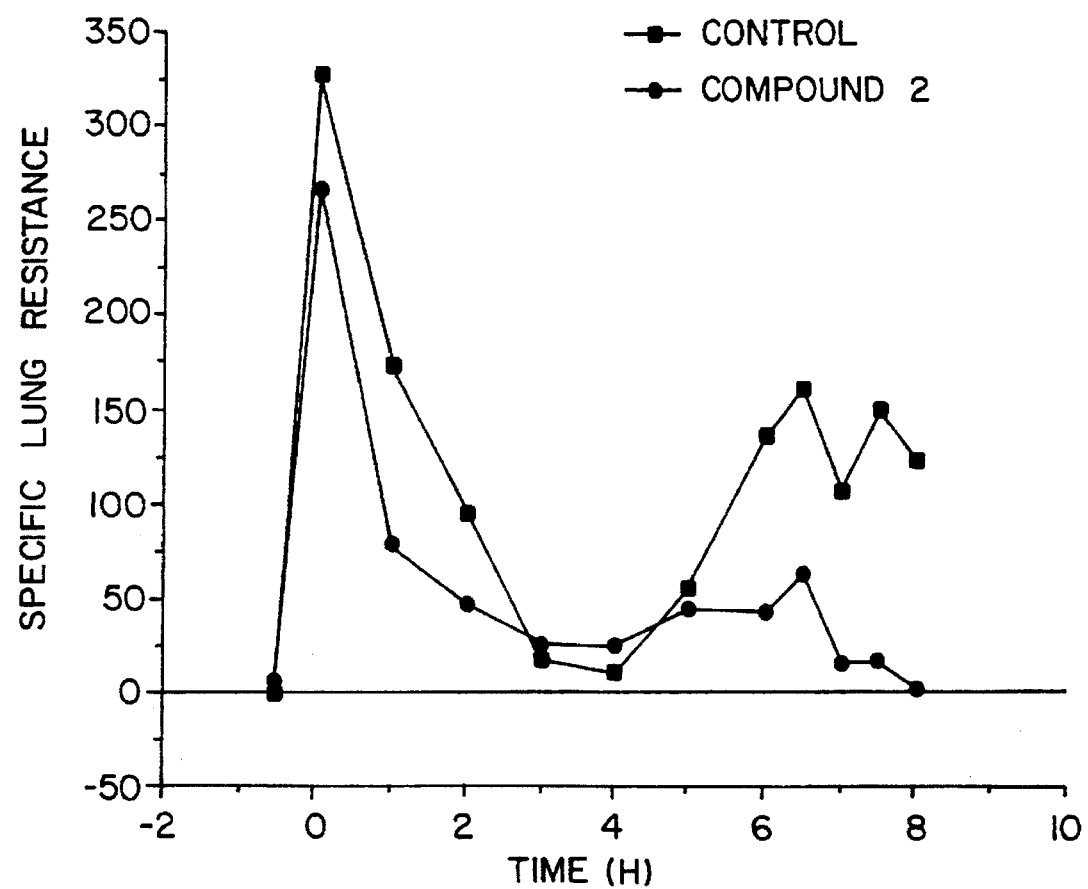
FIG. 5 is a graphical representation of the Specific Lung Resistance (SRL) as a function of time (in hours) of antigen-challenged sheep treated with N,N'-bis(4-guanidylbenzylaminecarbonylmethylene)-1,4-benzenedimethanol dicarbamate, Compound 2 of Table II, of the invention in an orally delivered composition and sheep treated with a control.

Compound 2 was also found to possess oral activity. Three doses of Compound 2 (40 mg in 60 mL water) were administered to sheep through an intergastric tube 1 hr before challenge, 4 hours post-challenge, and 24 hours post-challenge. As illustrated in FIG. 5, animals treated with Compound 11 had an early phase SRL of about 270. Untreated animals showed an SRL of about 350. With respect to late phase reaction, animals treated with Compound 2 showed an SRL of about 70 as compared to an SRL of over 150 for untreated animals. Thus, Compound 2 showed significant anti-asthmatic properties when delivered orally.

Thus, the present invention provides compounds and compositions that are useful for the prevention and treatment of immunomediated inflammatory disorders, particularly those associated with the respiratory tract, including asthma, and the hyperresponsiveness phase associated with chronic asthma, in addition to allergic rhinitis. The present invention is also recognized as providing a method for treating immunomediated inflammatory disorders that are susceptible to treatment with a tryptase inhibitor of the present invention.

The disclosures in this application of all articles and references, including patents and patent applications, are incorporated herein by reference.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A compound effective to inhibit tryptase activity comprising the structure:

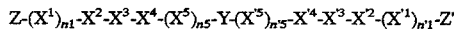

and its pharmaceutically acceptable salts, wherein:

Y is aryl or substituted aryl;

Z and Z' independently are

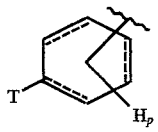

where T is $-CH_2NH_2$ or $-NHC(NH)NH_2$; and p is an even integer between 4 and i0 inclusive;

$X^1$, $X'^1$, $X^5$, and $X'^5$ are methylene or substituted methylene, and $n_1$, $n'_1$, $n_5$ and $n'_5$ independently are 0 or 1;

$X^2$, $X'^2$, $X^4$, and $X'^4$ are selected independently from the group consisting of -NRC(O)-, -NRC(O)NR'-, -NRC(O)O-, -C(O)NR- and -OC(O)NR-, wherein R and R' are selected independently from the group consisting of hydrogen, lower alkyl, aryl, substituted lower alkyl, substituted aryl, aralkyl and substituted aralkyl; and $X^3$ and $X'^3$, are selected independently from the group consisting of cycloalkylene, cycloheteroalkylene, substituted cycloalkylene, substituted cycloheteroalkylene, lower alkylene and substituted lower alkylene.

2. The compound of claim 1, wherein Z is 4-aminomethylphenyl.

3. The compound of claim 2, wherein Z' is 4-aminomethylphenyl.

4. The compound of claim 2, wherein Z' is 4-aminomethylcyclohexyl.

5. The compound of claim 2, wherein Z' is 4-guanidylphenyl.

6. The compound of claim 2, wherein Z' is 4-guanidylcyclohexyl.

7. The compound of claim 2, wherein $n_1$ and $n'_1$ are both 1, $X^1$ and $X'^1$ are both methylene, $X^2$ is -NHC(O)- and $X'^2$ is -C(O)NH-.

8. The compound of claim 7, wherein $X^3$ and $X'^3$ are selected independently from the group consisting of methylene, ethylene, and propylene.

9. The compound of claim 2, wherein $n_1$ and $n'_1$ are both 0 and $X^2$ is -C(O)NH-, and $X'^2$ is -NHC(O)-.

10. The compound of claim 9, wherein $X^3$ and $X'^3$ are selected independently from the group consisting of methylene, ethylene, and propylene.

11. The compound of claim 10, wherein Y is 1,3- or 1,4-phenylene or substituted phenylene.

12. The compound of claim 11, which is selected from the group consisting of:

N,N'-bis(4-aminomethylbenzamidopropylene)-1,4-benzenedimethanol dicarbamate,

N,N'-bis(N-(4-aminomethylbenzamido)-4-aminobutyric)-p-xylylene diamide,

N,N'-bis(4-aminomethylbenzamidoethylene)-1,4-benzenedimethanol dicarbamate,

N,N'-bis(4-aminomethylbenzamidobutyl)-terephthalyldiamide.

13. The compound of claim 1, wherein Y is 1,3- or 1,4-phenylene or substituted phenylene.

14. The compound of claim 13, which is selected from the group consisting of:

N,N'-bis(N-(4-aminomethylbenzyl)succinamido)-p-xylylene diamide,

N,N'-bis(N-(4-aminomethylbenzyl)malonamido)-p-xylylene diamide,

N,N'-bis(N-aminomethylbenzyl)glutaramido)-p-xylylene diamide,

N,N'-bis(N-(3-aminomethylbenzyl)succinamido)-m-xylylene diamide,

N,N'-(bis(methyl)-bis(N-(4-aminomethylbenzyl)succinamido)-p-xylylene diamide,

N,N'-bis(N-(4-aminomethylbenzyl)glutaramido)-N,N'-bis(methyl)-p-xylylene diamide, N,N'-bis(N-(3-aminomethylbenzyl)succinamido)-p-xylylene diamide, N,N'-bis(N-(3-aminomethylbenzyl)succinamido)-m-xylylene diamide, bis(p-xylylenediamineglycine)-1,4-benzene-dimethanol dicarbamate, N-(3-aminomethylbenzylsuccinamido)-N'-(4-aminomethyl-benzylsuccinamido)-p-xylylene diamide, N-(3-aminomethylbenzylsuccinamido)-N'-(4-aminomethyl-benzylsuccinamido)-m-xylylene diamide, bis(p-xylylenediaminesarcosine)-1,4-benzene-dimethanol dicarbamate, bis(1,4-cyclohexyldimethylamine-N-methyl-N-glycine)-1,4-benzenedimethanol dicarbamate, bis(p-xylylenediamine-D-alanine)-1,4-benzene-dimethanol dicarbamate, bis(p-xylylenediamine-L-alanine)-1,4-benzene-dimethanol dicarbamate, N,N,-bis(N-(4-aminomethylbenzyl)butyramido)-terephthalamide, N,N,-bis(N-(4-aminomethylbenzyl)butyramido)-N,N'-bis(methyl)-terephthalamide, N,N,-bis((N-(4-aminomethylbenzyl)succinamido))-p-phenethylene diamide, bis((4-aminomethylanilido)glycine)-1,4-benzenedimethanol dicarbamate, bis((4-guanidomethylanilido)glycine)-1,4-benzenedimethanol dicarbamate, bis((3-aminomethylbenzylamido)glycine)-1,4-benzenedimethanol dicarbamate, bis(N-(4-aminomethylbenzyl)glycyl urea)-p-xylylene diamide, bis(N-(4-aminomethylbenzyl)glycyl urea)-1,4-phenethylene diamide, N,N'-bis(methyl)-bis(glycine-trans-1,4-cyclohexylbis (methylamine)urea)-p-xylylene diamide, N,N'-bis(methyl)-bis(glycine-p-xylylenediamine urea)-p-xylylene diamide, N,N'-bis(methyl)-bis(4-aminomethylbenzoyl-trans-1,4-cyclohexylbis)methylamine)urea)xylylene diamide, and N,N'-bis(methyl)-bis(sarcosine-trans-1,4-cyclohexylbis (methylamine)urea)-p-xylylene diamide.

15. The compound of claim 1, wherein Z is 4-guanidylphenyl.

16. The compound of claim 15, wherein $n_1$ and $n'_1$ are both 1, and $X^1$ and $X'^1$ are both methylene.

17. The compound of claim 16, wherein $X^3$ and $X'^3$ are selected independently from the group consisting of methylene, ethylene, and propylene.

18. The compound of claim 17, wherein Y is 1,3- or 1,4-phenylene or substituted phenylene.

19. The compound of claim 18 is selected from the group consisting of:

N,N'-bis(N-(4-guanidylbenzylamine)malonamido)-p-xylylene diamide,

N,N'-bis(N-(4-guanidylbenzylamino)succinamido-p-xylylene diamide,

N,N'-bis(N-(4-guanidylbenzylamino)glutaramido-p-xylylene diamide,

N,N'-bis(4-guanidylbenzylaminecarbonylethylene)-1,4-benzenedimethanol dicarbamate, N,N'-bis(4-(guanidylbenzylaminecarbonylmethylene)-1,4-benzenedimethanol dicarbamate, bis((4-guanidylbenzyl)-L-phenylalanineamide-$N^{\alpha}$-carbonyl)-1,4-dimethanolbenzene, bis((4-guanidylbenzyl)-L-prolineamide-$N^{\alpha}$-carbonyl)-1,4-dimethanolbenzene, bis((4-guanidylbenzyl)-L-alanineamide-$N^{\alpha}$-carbonyl)-1,4-dimethanolbenzene, bis((4-guanidylbenzyl)-D-alanineamide-$N^{\alpha}$-carbonyl)-1,4-dimethanolbenzene, bis((R,S)-2-(2-(4-guanidinobenzylamino)-2,3-dehydro-6-piperidone)-1,4-benzenedimethanol dicarbamate, bis((R,S)-2-(2-(4-guanidinobenzylamino)-2,3-dehydro-6-piperidone)-1,4-benzenedimethanol dicarbamate, 4-(guanidinobenzylamido)glycine-1,4-xylylene diurea, and N,N-bis((4-guanidobenzyluriedo)acetyl)]-1,4-xylylene diamide.

20. The compound of claim 1, wherein Z is 4-aminomethylcyclohexyl.

21. The compound of claim 20, wherein $n_1$ and $n'_1$ are both 1, $X^1$ and $X'^1$ are both methylene, $X^2$ is -C(O)NH-, and $X'^2$ is -NHC(O) -.

22. The compound of claim 21, wherein $X^3$ and $X'^3$ are selected independently from the group consisting of methylene, ethylene, and propylene.

23. The compound of claim 22, wherein Y is 1,3- or 1,4-phenylene or substituted phenylene.

24. The compound of claim 23 is selected from the group consisting of:

N,N'-bis(N-(4-aminomethylcyclohexylmethyl)-glutaramido)-p-xylylene diamide,

N,N'-bis(methyl)-bis(N-(4-aminomethylcyclohexylmethyl)-succinamido)-p-xylylene diamide, N,N'-bis(N-(4-aminomethylcyclohexylmethyl)-succinamido)-p-xylylene diamide, N,N'-bis(methyl)-bis(N-(4-aminomethylcyclohexylmethyl)-glutaramido)-p-xylylene diamine, bis(1,4-cyclohexyldimethylamineglycine)-1,4-benzenedimethanol dicarbamate, and bis(trans-1,4-cyclohexyldimethylamineglycine)-1,4-benzenedimethanol dicarbamate.

25. The compound of claim 20, wherein $n_1$ and $n'_1$ are both 0 $X^2$ is -C(O)NH-, and $X'^2$ is -NHC(O)-.

26. The compound of claim 25, wherein $X^3$ and $X'^3$ are selected independently from the group consisting of methylene, ethylene, and propylene.

27. The compound of claim 26, wherein Y is 1,3- or 1,4-phenylene or substituted phenylene.

28. The compound of claim 27 is selected from the group consisting of:

N,N'-bis(trans-4-aminomethylcyclohexyl-1-amido propylene)-1,4-benzenedimethanol dicarbamate, N,N'-bis(trans-4-aminomethylcyclohexyl-1-amidobutyl)-1,4-benzenedimethanol dicarbamate, and bis-[4-N-(4-(aminomethyl)cyclohexylamido)butyroyl)]-1,4-xylylene diamide.

29. An aerosol composition for the treatment of immunomediated inflammatory disorders comprising at least one compound of claim 1 in an aerosolized pharmaceutically acceptable carrier or solution or dry powder.

30. The composition of claim 29, wherein said compound is a compound of claim 10, claim 14, claim 19, claim 24 or claim 28.

31. The composition of claim 29 wherein said inflammatory disorder is asthma.

32. The composition of claim 29 wherein said inflammatory disorder is allergic rhinitis.

33. The composition of claim 29 wherein said compound is present in a pharmaceutically acceptable carrier solution at a concentration between about 0.1 to 30 mg/ml.

34. The composition of claim 29 further comprising a β-adrenergic agonist compound.

35. The composition of claim 34 wherein said β-adrenergic agonist compound is selected from the group consisting of albuterol, terbutaline, formoterol, fenoterol, and prenaline.

36. The composition of claim 29 further comprising an anti-inflammatory corticosteroid.

37. The composition of claim 36 wherein said anti-inflammatory corticosteroid is selected from the group consisting of beclomethasone, triamcinolone, flurisolide, and dexamethasone.

38. A pharmaceutical composition comprising at least one compound of claim 1 in combination with a pharmaceutically acceptable carrier.

39. The composition of claim 38, wherein said compound is a compound of claim 10, claim 14, claim 19, claim 24 or claim 28.

40. The composition of claim 38 wherein the pharmaceutically acceptable carrier comprises a pharmaceutically acceptable topical carrier.

41. An oral composition for the treatment of immunomediated inflammatory disorders, comprising at least one compound of claim 1 in a pharmaceutically acceptable oral carrier solution.

42. The composition of claim 41, wherein said compound is N,N'-bis(4-guanidylbenzylaminecarbonylmethylene)-1,4-benzenedimethanol dicarbamate.

* * * * *